United States Patent
Cotsarelis et al.

(10) Patent No.: US 12,214,014 B2
(45) Date of Patent: Feb. 4, 2025

(54) METHODS FOR SCAR REDUCTION BY CONVERTING SCAR FIBROBLASTS INTO ADIPOCYTES WITH HAIR FOLLICLE-DERIVED SIGNALS

(71) Applicant: The Trustees of the University of Pennsylvania, Philadelphia, PA (US)

(72) Inventors: George Cotsarelis, Berwyn, PA (US); Christian F. Guerrero-Juarez, Redlands, CA (US); Maksim Plikus, Irvine, CA (US)

(73) Assignees: The Trustees of the University of Pennsylvania, Philadelphia, PA (US); The Regents of the University of California, Oakland, CA (US)

( * ) Notice: Subject to any disclaimer, the term of this patent is extended or adjusted under 35 U.S.C. 154(b) by 178 days.

(21) Appl. No.: 16/475,570

(22) PCT Filed: Jan. 3, 2018

(86) PCT No.: PCT/US2018/012266
§ 371 (c)(1),
(2) Date: Jul. 2, 2019

(87) PCT Pub. No.: WO2018/129101
PCT Pub. Date: Jul. 12, 2018

(65) Prior Publication Data
US 2020/0121760 A1    Apr. 23, 2020

Related U.S. Application Data

(60) Provisional application No. 62/442,321, filed on Jan. 4, 2017.

(51) Int. Cl.
| | |
|---|---|
| *A61K 38/18* | (2006.01) |
| *A61K 9/00* | (2006.01) |
| *A61K 35/36* | (2015.01) |
| *A61K 45/06* | (2006.01) |
| *A61P 17/02* | (2006.01) |

(52) U.S. Cl.
CPC ........ *A61K 38/1875* (2013.01); *A61K 9/0014* (2013.01); *A61K 9/0021* (2013.01); *A61K 35/36* (2013.01); *A61K 45/06* (2013.01); *A61P 17/02* (2018.01)

(58) Field of Classification Search
None
See application file for complete search history.

(56) References Cited

U.S. PATENT DOCUMENTS

| | | | | |
|---|---|---|---|---|
| 6,150,328 A | * | 11/2000 | Wang | ............. A61L 27/227 514/8.8 |
| 7,786,080 B2 | * | 8/2010 | Muller | ............. A61P 27/02 530/350 |
| 2005/0233450 A1 | | 10/2005 | Goetinck et al. | |
| 2006/0122109 A1 | * | 6/2006 | Cho | ............. A61P 43/00 514/8.8 |
| 2006/0286157 A1 | * | 12/2006 | Akella | ............. A61P 17/02 514/474 |
| 2007/0293425 A1 | | 12/2007 | Muller et al. | |
| 2011/0321180 A1 | | 12/2011 | Lee et al. | |

FOREIGN PATENT DOCUMENTS

WO   WO-2015/089050    6/2015

OTHER PUBLICATIONS

Schulz et al. Emerging Role of Bone Morphogenetic Proteins in Adipogenesis and Energy 16-17,21,23/21—Metabolism. Cytokine Growth Factor Rev. 2009, (5-6): 523-531; p. 7. third paragraph. DOI:10.1016/j.cytogfr.2009.10.019.
Zhang, et al; "Intralesional injection of adipose-derived stem cells reduces hypertrophic scarring in a rabbit ear model" —Stem Cell Research & Therapy (2015) 6: 145.
Bitter et al., "[33] Expression and secretion vectors for yeast." Methods in enzymology 153 (1987):516-544.
Brisson et al., "Expression of a bacterial gene in plants by using a viral vector." Nature 310.5977 (1984):511-514.
Brogli et al., Light-regulated expression of a pea ribulose-1,5-bisphosphate carboxylase small subunit gene in transformed plant cells. Science 224 (1984).
Coruzzi, et al. "Tissue-specific and light-regulated expression of a pea nuclear gene encoding the small subunit of ribulose-1, 5-bisphosphate carboxylase." The EMBO Journal 3.8 (1984): 1671-1679.
Gay, et al. "Fgf9 from dermal γδ T cells induces hair follicle neogenesis after wounding." Nature medicine 19.7 (2013): 916-923.
Gurley, et al. "Upstream sequences required for efficient expression of a soybean heat shock gene." Molecular and cellular biology 6.2 (1986): 559-565.
International Preliminary Report on Patentability from PCT/US2018/12266 dated Jul. 18, 2019.

(Continued)

*Primary Examiner* — Elizabeth C. Kemmerer
(74) *Attorney, Agent, or Firm* — Mark S. Cohen; PEARL COHEN ZEDEK LATZER BARATZ LLP

(57) ABSTRACT

This invention describes methods for treating wound healing pathologies, inhibiting or reversing fibrotic skin disorders, including but not limited to keloids, atrophic and hypertrophic scars, and reversing skin aging via generating new dermal adipocytes (DAs). Methods described herein comprise (a) grafting of human hair follicles or (b) direct delivery of conditioned media from in vitro cultured hair follicles, or (c) delivery of purified individual factors secreted by hair follicles, or (d) delivery of small molecule agonists that mimic hair derived signaling activities, or (e) delivery of small molecule antagonists that inhibit anti-adipogenic programs, or (f) delivery of small molecule agonists of pro-adipogenic programs to convert endogenous wound or scar skin fibroblasts into new DAs.

10 Claims, 23 Drawing Sheets
Specification includes a Sequence Listing.

(56) References Cited

OTHER PUBLICATIONS

International Search Report and Written Opinion from PCT/US2018/12266 dated Jul. 5, 2018.
Ishibashi, et al. "An Evi1-C/EBPβ complex controls peroxisome proliferator-activated receptor Y2 gene expression to initiate white fat cell differentiation." Molecular and cellular biology 32.12 (2012): 2289-2299.
Picelli, et al. "Full-length RNA-seq from single cells using Smart-seq2." Nature protocols 9.1 (2014): 171-181.
Picelli, et al. "Smart-seq2 for sensitive full-length transcriptome profiling in single cells." Nature methods 10.11 (2013): 1096-1098.
Remington's Pharmaceutical Sciences, Mack Publishing Co., 16th ed. (1980).
Studier, F. William. "Use of T7 RNA polymerase to direct expression of cloned genes." Methods Enzymol. 185 (1990): 60-89.
Takamatsu, et al. "Expression of bacterial chloramphenicol acetyltransferase gene in tobacco plants mediated by TMV-RNA." The EMBO Journal 6.2 (1987): 307-311.
Vangipuram, et al. "Skin punch biopsy explant culture for derivation of primary human fibroblasts." Journal of visualized experiments: JoVE 77 (2013). Abstract.
Weissbach & Weissbach, 1988, Methods for Plant Molecular Biology, Academic Press, NY, Section VIII, pp. 421.

\* cited by examiner

```
                       SEQUENCE LISTING

<160> NUMBER OF SEQ ID NOS: 38

<210> SEQ ID NO 1
<211> LENGTH: 18
<212> TYPE: DNA
<213> ORGANISM: Mus Musculus

<400> SEQUENCE: 1
gaaggtgaag gtcggagt                                                 18

<210> SEQ ID NO 2
<211> LENGTH: 20
```

```
<212> TYPE: DNA
<213> ORGANISM: Mus musculus

<400> SEQUENCE: 2
gaagatggtg atgggatttc                                               20

<210> SEQ ID NO 3
<211> LENGTH: 22
<212> TYPE: DNA
<213> ORGANISM: Mus musculus

<400> SEQUENCE: 3
gcactggcaa gttctactgc aa                                            22

<210> SEQ ID NO 4
<211> LENGTH: 23
<212> TYPE: DNA
<213> ORGANISM: Mus musculus

<400> SEQUENCE: 4
gtaggtgaag agaacggcct tgt                                           23

<210> SEQ ID NO 5
<211> LENGTH: 23
<212> TYPE: DNA
<213> ORGANISM: Mus musculus

<400> SEQUENCE: 5
ctgtccagtc tatccttgca cac                                           23

<210> SEQ ID NO 6
<211> LENGTH: 21
<212> TYPE: DNA
<213> ORGANISM: Mus musculus

<400> SEQUENCE: 6
cagaaggcac agcagtcttg a                                             21

<210> SEQ ID NO 7
<211> LENGTH: 21
<212> TYPE: DNA
<213> ORGANISM: Mus musculus

<400> SEQUENCE: 7
gtgccagttt cgatccgtag a                                             21

<210> SEQ ID NO 8
<211> LENGTH: 20
<212> TYPE: DNA
<213> ORGANISM: Mus musculus

<400> SEQUENCE: 8
ggccagcatc gtgtagatga                                               20

<210> SEQ ID NO 9
<211> LENGTH: 20
<212> TYPE: DNA
<213> ORGANISM: Mus musculus

<400> SEQUENCE: 9
agagtgccaa caccagttcc                                               20

<210> SEQ ID NO 10
```

-continued

```
<211> LENGTH: 20
<212> TYPE: DNA
<213> ORGANISM: Mus musculus

<400> SEQUENCE: 10
acgaggtcat ttttcgttgg                                                  20

<210> SEQ ID NO 11
<211> LENGTH: 20
<212> TYPE: DNA
<213> ORGANISM: Mus musculus

<400> SEQUENCE: 11
acggctccag caagaacaag                                                  20

<210> SEQ ID NO 12
<211> LENGTH: 20
<212> TYPE: DNA
<213> ORGANISM: Mus musculus

<400> SEQUENCE: 12
ttgtgcagat gcgggtactg                                                  20

<210> SEQ ID NO 13
<211> LENGTH: 19
<212> TYPE: DNA
<213> ORGANISM: Mus musculus

<400> SEQUENCE: 13
tggcctggga ttcctctgt                                                   19

<210> SEQ ID NO 14
<211> LENGTH: 21
<212> TYPE: DNA
<213> ORGANISM: Mus musculus

<400> SEQUENCE: 14
ttgtcgcact gttcagttct c                                                21

<210> SEQ ID NO 15
<211> LENGTH: 20
<212> TYPE: DNA
<213> ORGANISM: Mus musculus

<400> SEQUENCE: 15
gccctgcagt ccttcgctgg                                                  20

<210> SEQ ID NO 16
<211> LENGTH: 20
<212> TYPE: DNA
<213> ORGANISM: Mus musculus

<400> SEQUENCE: 16
ctgacgtgct ggccctggtg                                                  20

<210> SEQ ID NO 17
<211> LENGTH: 20
<212> TYPE: DNA
<213> ORGANISM: Mus musculus

<400> SEQUENCE: 17
acgtggtgaa gcatcgtact                                                  20
```

```
<210> SEQ ID NO 18
<211> LENGTH: 20
<212> TYPE: DNA
<213> ORGANISM: Mus musculus

<400> SEQUENCE: 18
ggccatgaga aggtaaggtt                                                    20

<210> SEQ ID NO 19
<211> LENGTH: 25
<212> TYPE: DNA
<213> ORGANISM: Mus musculus

<400> SEQUENCE: 19
gatttcagga aagcccaaca aagaa                                              25

<210> SEQ ID NO 20
<211> LENGTH: 23
<212> TYPE: DNA
<213> ORGANISM: Mus musculus

<400> SEQUENCE: 20
gttggatctg ccatgatgcc ttt                                                23

<210> SEQ ID NO 21
<211> LENGTH: 20
<212> TYPE: DNA
<213> ORGANISM: Mus musculus

<400> SEQUENCE: 21
caccaagagc agccacctca                                                    20

<210> SEQ ID NO 22
<211> LENGTH: 20
<212> TYPE: DNA
<213> ORGANISM: Mus musculus

<400> SEQUENCE: 22
cgggacactg gtacggcttc                                                    20

<210> SEQ ID NO 23
<211> LENGTH: 21
<212> TYPE: DNA
<213> ORGANISM: Mus musculus

<400> SEQUENCE: 23
cgactacatc agggacctgc a                                                  21

<210> SEQ ID NO 24
<211> LENGTH: 18
<212> TYPE: DNA
<213> ORGANISM: Mus musculus

<400> SEQUENCE: 24
gaacacatgc cgcctcgg                                                      18

<210> SEQ ID NO 25
<211> LENGTH: 21
<212> TYPE: DNA
<213> ORGANISM: Mus musculus

<400> SEQUENCE: 25
aaggactgcc agaaaaagga c                                                  21
```

```
<210> SEQ ID NO 26
<211> LENGTH: 20
<212> TYPE: DNA
<213> ORGANISM: Mus musculus

<400> SEQUENCE: 26
gcagaaattg cctgagaagc                                              20

<210> SEQ ID NO 27
<211> LENGTH: 21
<212> TYPE: DNA
<213> ORGANISM: Homo sapiens

<400> SEQUENCE: 27
cccaacatgc ccattcgctt t                                            21

<210> SEQ ID NO 28
<211> LENGTH: 21
<212> TYPE: DNA
<213> ORGANISM: Homo sapiens

<400> SEQUENCE: 28
acagcccagg aatgttgcag t                                            21

<210> SEQ ID NO 29
<211> LENGTH: 21
<212> TYPE: DNA
<213> ORGANISM: Homo sapiens

<400> SEQUENCE: 29
tggaggtggg tgcttgtagt t                                            21

<210> SEQ ID NO 30
<211> LENGTH: 21
<212> TYPE: DNA
<213> ORGANISM: Homo sapiens

<400> SEQUENCE: 30
ggtgcaatca caactcactg c                                            21

<210> SEQ ID NO 31
<211> LENGTH: 23
<212> TYPE: DNA
<213> ORGANISM: Homo sapiens

<400> SEQUENCE: 31
gtcatgaaag gcgtcacttc cac                                          23

<210> SEQ ID NO 32
<211> LENGTH: 23
<212> TYPE: DNA
<213> ORGANISM: Homo sapiens

<400> SEQUENCE: 32
caatgcgaac ttcagtccag gtc                                          23

<210> SEQ ID NO 33
<211> LENGTH: 23
<212> TYPE: DNA
<213> ORGANISM: Homo sapiens

<400> SEQUENCE: 33
gcaggagatc acagagtatg cca                                          23
```

```
<210> SEQ ID NO 34
<211> LENGTH: 21
<212> TYPE: DNA
<213> ORGANISM: Homo sapiens

<400> SEQUENCE: 34
tcaaggaggc cagcattgtg t                                                  21

<210> SEQ ID NO 35
<211> LENGTH: 21
<212> TYPE: DNA
<213> ORGANISM: Homo sapiens

<400> SEQUENCE: 35
tgcagaatcc acgccagtac a                                                  21

<210> SEQ ID NO 36
<211> LENGTH: 23
<212> TYPE: DNA
<213> ORGANISM: Homo sapiens

<400> SEQUENCE: 36
atcttcttca gtcgctccag gtc                                                23

<210> SEQ ID NO 37
<211> LENGTH: 21
<212> TYPE: DNA
<213> ORGANISM: Homo sapiens

<400> SEQUENCE: 37
ccaaatccac gttgccaacc a                                                  21

<210> SEQ ID NO 38
<211> LENGTH: 23
<212> TYPE: DNA
<213> ORGANISM: Homo sapiens

<400> SEQUENCE: 38
tgctcaatga ggtgacagag gag                                                23
```

METHODS FOR SCAR REDUCTION BY CONVERTING SCAR FIBROBLASTS INTO ADIPOCYTES WITH HAIR FOLLICLE-DERIVED SIGNALS

CROSS-REFERENCE TO RELATED APPLICATIONS

The subject Application is a U.S. national stage application under 37 U.S.C. 371 of PCT International Application PCT/US2018/012266, filed 3 Jan. 2018, which claims priority to U.S. Provisional Application No. 62/442,321, filed 4 Jan. 2017, the entire contents of which are hereby incorporated by reference in their entirety.

GOVERNMENT INTEREST STATEMENT

This invention was supported by Grant Numbers R01-AR055309, R01-AR067273, R01-AR069653, P30-AR057217, DK49210, GM055246, and T32-CA009054-37 from the NIH and DGE-1321846 from the NSF. The United States government has certain rights in the invention.

FIELD OF THE INVENTION

The invention relates to pharmaceutical compositions and methods for treating wound healing pathologies and aging, and regeneration of dermal adipocytes (DAs). Specifically, the invention relates to (a) canonical WNT pathway antagonists, (b) non-canonical WNT pathway ligands, (c) FGF pathway ligands, (d) BMP pathway ligands, (e) HH pathways ligands, (f) Asip, (g) Serpinfl polypeptides, (h) Insulin, and (i) IGF pathway ligands, and administering canonical WNT pathway members; non-canonical WNT pathway members; FGF pathway members; BMP pathway members; SHH pathway members; PPARy agonists, such as rosiglitazone or pioglitazone; and bone morphogenetic protein (BMP)-2/4/7 (i.e., bone morphogenetic protein 2 (BMP2), or bone morphogenetic protein 4 (BMP4), or bone morphogenetic protein 7 (BMP7), or a combination thereof), and ASIP, and SERPINF1, and WISP2, and WIF1, and IGFBP2, and IGFBP6 polypeptides for treating wound healing pathologies and aging via regenerating new DAs.

BACKGROUND OF THE INVENTION

Wound healing is a multi-step process that culminates with formation of a scar. In some instances, these repair processes go awry and lead to wound healing pathologies. Keloids are benign, scar overgrowths that are a deviation of the normal wound healing process. No single therapy is available for keloid treatment although surgery and intralesional corticosteroids can transiently improve keloids. However, keloids almost universally recur and often end up larger than before treatment. Therefore, the conversion of keloid fibroblasts, which are constituted of dense collagen, to other cell types found in normal skin, such as the softer and less dense dermal adipocytes (DAs), is desirable in the treatment of keloids as well as other wound healing pathologies, including but not limited to hypertrophic (HS), and atrophic scars (AS), as well as natural or accelerated skin aging manifested by the loss of endogenous DAs.

SUMMARY OF THE INVENTION

The invention relates to pharmaceutical compositions and methods for treating wound healing pathologies, inhibiting or reversing fibrotic skin disorders, including but not limited to to keloids, atrophic and hypertrophic scars, and reversing skin aging.

In one aspect, provided herein are methods for treating wound healing pathologies characterized by abnormal proliferation of mesenchymal scar tissue; treating, inhibiting, or suppressing a degenerative lipodistrophic skin disorder; treating keloid scars (KS), and other wound healing pathologies; and skin aging in a subject and generating new dermal adipocytes (DAs), by administering BMP-2/4/7 (i.e., bone morphogenetic protein 2 (BMP2), or bone morphogenetic protein 4 (BMP4), or bone morphogenetic protein 7 (BMP7), or a combination thereof) polypeptides; conditioned media from in vitro cultured hair follicles; or any other compound that upregulates hair derived signaling activities, including canonical WNT pathway antagonists; non-canonical WNT pathway ligands; FGF pathway ligands; BMP pathway ligands; HH pathway ligands; PPARy agonists, such as rosiglitazone or pioglitazone; Insulin; IGF pathway ligands; and ASIP, and SERPINF1, and WISP2, and WIF1, and IGFBP2, and IGFBP6 polypeptides; or by grafting of human hair follicles to, into, or on human wounds or scars. Also, provided herein are compositions for treating wound healing pathologies characterized by abnormal proliferation of mesenchymal scar tissue; treating, inhibiting, or suppressing a degenerative lipodistrophic skin disorder; treating keloid scars (KS), and other wound healing pathologies; and skin aging in a subject and generating new dermal adipocytes (DAs), comprising BMP-2/4/7 polypeptides (i.e., bone morphogenetic protein 2 (BMP2), or bone morphogenetic protein 4 (BMP4), or bone morphogenetic protein 7 (BMP7), or a combination thereof); conditioned media from in vitro cultured hair follicles; or any other compound that upregulates hair derived signaling activities, including canonical WNT pathway antagonists; non-canonical WNT pathway ligands; FGF pathway ligands; BMP pathway ligands; HH pathway ligands; PPARγ agonists, such as rosiglitazone or pioglitazone; Insulin; IGF pathway ligands; and ASIP, and SERPINF1, and WISP2, and WIF1, and IGFBP2, and IGFBP6 polypeptides.

In one aspect, the invention relates to (a) grafting of human hair follicles or (b) direct delivery of conditioned media from in vitro cultured hair follicles, or (c) delivery of purified individual factors secreted by hair follicles, or (d) delivery of small molecule agonists that mimic hair derived signaling activities, or (e) delivery of small molecule antagonists that inhibit anti-adipogenic programs, or (f) delivery of small molecule agonists of pro-adipogenic programs with the goal of treating wound healing pathologies, inhibiting or reversing fibrotic skin disorders, including but not limited to keloids, atrophic and hypertrophic scars, and reversing skin aging by converting endogenous wound or scar skin fibroblasts into new DAs.

Other features and advantages of the present invention will become apparent from the to following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

Figure 1:
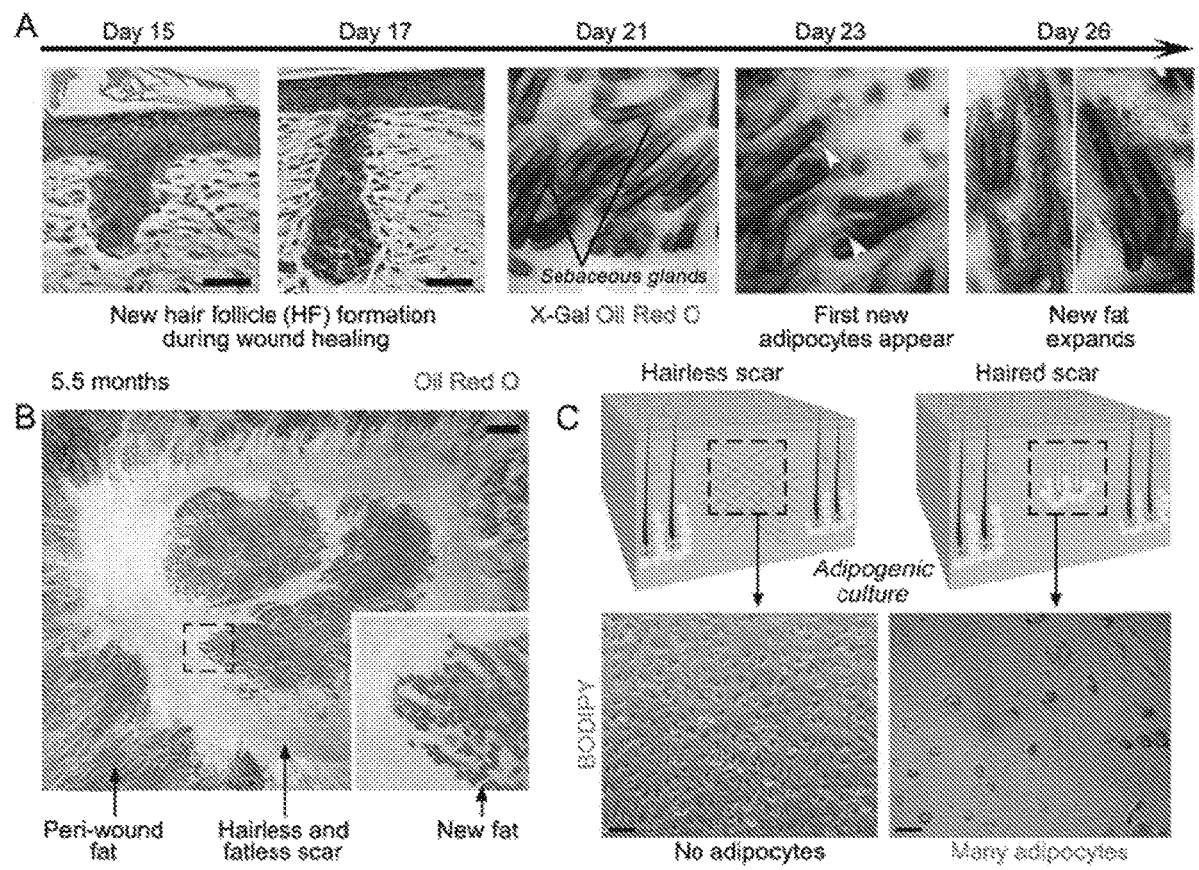
FIG. 1: New adipocytes only regenerate around new hair follicles during wound healing. (A) Histological sections and wholemount images (3 right panels) of skin stained to detect follicular epithelium (blue) and adipocytes (orange) in K14-Cre;R26R mice at indicated post wounding days. New adipocytes (arrowheads) increase in number and size over several days. (B) Skin viewed from the undersurface. New adipocytes form and persist exclusively around regenerated hair follicles, which arise in the center of the wound. (C) Cultured dermal cells isolated from wounds with regenerated hair follicles differentiated into Bodipy-positive (green) adipocytes, whereas cultured dermal cells from wounds lacking follicles formed no adipocytes. Size bars: A, C—20 µm; B—1 mm.

The invention relates to pharmaceutical compositions and methods for treating wound healing pathologies, inhibiting or reversing fibrotic skin disorders, including but not limited to keloids, atrophic and hypertrophic scars, and reversing skin aging.

In one aspect, provided herein are methods for treating wound healing pathologies characterized by abnormal proliferation of mesenchymal scar tissue; treating, inhibiting, or suppressing a degenerative lipodistrophic skin disorder; treating keloid scars (KS), and other wound healing pathologies; and skin aging in a subject and generating new dermal adipocytes (DAs), by administering BMP-2/4/7 (i.e., bone morphogenetic protein 2 (BMP2), or bone morphogenetic protein 4 (BMP4), or bone morphogenetic protein 7 (BMP7), or a combination thereof) polypeptides; conditioned media from in vitro cultured hair follicles; or any other compound that upregulates hair derived signaling activities, including canonical WNT pathway antagonists; non-canonical WNT pathway ligands; FGF pathway ligands; BMP pathway ligands; HH pathway ligands; PPARγ agonists, such as rosiglitazone or pioglitazone; Insulin; IGF pathway ligands; and ASIP, and SERPINF1, and WISP2, and WIF1, and IGFBP2, and IGFBP6 polypeptides, or by grafting of human hair follicles to, into, or on human wounds or scars. Also, provided herein are compositions for treating wound healing pathologies characterized by abnormal proliferation of mesenchymal scar tissue; treating, inhibiting, or suppressing a degenerative lipodistrophic skin disorder; treating keloid scars (KS), and other wound healing pathologies; and skin aging in a subject and generating new dermal adipocytes (DAs), comprising BMP-2/4/7 (i.e., bone morphogenetic protein 2 (BMP2), or bone morphogenetic protein 4 (BMP4), or bone morphogenetic protein 7 (BMP7), or a combination thereof) polypeptides; conditioned media from in vitro cultured hair follicles; or any other compound that upregulates hair derived signaling activities, including canonical WNT pathway antagonists; non-canonical WNT pathway ligands; FGF pathway ligands; BMP pathway ligands; HH pathway ligands; PPARγ agonists, such as rosiglitazone or pioglitazone; Insulin; IGF pathway ligands; and ASIP, and SERPINF1, and WISP2, and WIF1, and IGFBP2, and IGFBP6 polypeptides.

In one aspect, the invention relates to (a) grafting of human hair follicles or (b) direct delivery of conditioned media from in vitro cultured hair follicles, or (c) delivery of purified individual factors secreted by hair follicles, or (d) delivery of small molecule agonists that mimic hair derived signaling activities, or (e) delivery of small molecule antagonists that inhibit anti-adipogenic programs, or (f) delivery of small molecule agonists of pro-adipogenic to programs with the goal of treating wound healing pathologies, inhibiting or reversing fibrotic skin disorders, including but not limited to keloids, atrophic and hypertrophic scars, and reversing skin aging by converting endogenous wound or scar skin fibroblasts into new DAs.

In one embodiment, the present invention provides methods for treating wound healing pathologies; inhibiting or reversing fibrotic skin disorders, including but not limited to, keloids, atrophic and hypertrophic scars; reversing skin aging; and improving wound and scar appearance.

In one embodiment, a composition or method of the present invention is utilized on human skin. In one embodiment, the composition or method is utilized on an area of unwanted scar overgrowth, including but not limited to, the earlobe, the cheek, the sternum, the shoulder, the chest, or the breast.

In one embodiment, the methods of the present invention include contacting a subject with conditioned media from in vitro cultured hair follicles, alone or in a composition with one or more additional compounds.

In one embodiment, the methods of the present invention include contacting a subject with any compound that upregulates adipogenesis lineage commitment pathways, alone or in a composition with one or more additional compounds.

In one embodiment, the methods of the present invention include grafting human hair follicles into a subject, alone or together with administering another compositions described herein.

In one embodiment, the methods of the present invention comprise the step of administering a composition comprising a bone morphogenetic protein 2 (BMP2) polypeptide, alone or in a composition with one or more additional compounds. BMP2 refers to BDA2, BMP2A. Amino acid sequences for BMP2 and nucleic acids that encode them are known in the art and can be obtained, for example, from GenBank.

In one embodiment, the methods of the present invention comprise the step of administering a composition comprising a bone morphogenetic protein 4 (BMP4) polypeptide, alone or in a composition with one or more additional compounds. BMP4 refers to ZYME, BMP2B, OFC11, BMP2B1, MCOPS6. Amino acid sequences for BMP4 and nucleic acids that encode them are known in the art and can be obtained, for example, from GenBank.

In one embodiment, the methods of the present invention comprise the step of administering a composition comprising a bone morphogenetic protein 7 (BMP7) polypeptide, alone or in a composition with one or more additional compounds. BMP7 refers to OP-1. Amino acid sequences for BMP7 and nucleic acids that encode them are known in the art and can be to obtained, for example, from GenBank.

In one embodiment, the methods of the present invention comprise the step of administering a composition comprising a LEPR polypeptide, alone or in a composition with one or more additional compounds. LEPR refers to OBR, OB-R, CD295, LEP-R, LEPRD, leptin receptor. Amino acid sequences for LEPR and nucleic acids that encode them are known in the art and can be obtained, for example, from GenBank.

In one embodiment, the methods of the present invention comprise the step of administering a composition comprising a WISP2 polypeptide, alone or in a composition with one or more additional compounds. WISP2 refers to CCN5, CT58, CTGF-L, WNTI inducible signaling pathway protein 2. Amino acid sequences for WISP2 and nucleic acids that encode them are known in the art and can be obtained, for example, from GenBank.

In one embodiment, the methods of the present invention comprise the step of administering a composition comprising a FSTL3 polypeptide, alone or in a composition with one or more additional compounds FSTL3 refers to FLRG, FSRP, follistatin-like 3. Amino acid sequences for FSTL3 and nucleic acids that encode them are known in the art and can be obtained, for example, from GenBank.

In one embodiment, the methods of the present invention comprise the step of administering a composition comprising an ASIP polypeptide, alone or in a composition with one or more additional compounds. ASIP refers to ASP, AGSW, AGTI, AGTIL, SHEP9, agouti signaling protein. Amino acid sequences for AGOUTI and nucleic acids that encode them are known in the art and can be obtained, for example, from GenBank.

In one embodiment, the methods of the present invention comprise the step of administering a composition comprising an INS, alone or in a composition with one or more additional compounds. INS refers to IDDM, ILPR, IRDN, IDDM1, IDDM2, MODY10, insulin. Amino acid sequences for INS and nucleic acids that encode them are known in the art and can be obtained, for example, from GenBank.

In one embodiment, the methods of the present invention comprise the step of administering a composition comprising an IGF1, alone or in a composition with one or more additional compounds. IGF1 refers to MGF, IGFI, IGF-I, insulin like growth factor 1. Amino acid sequences for IGF1 and nucleic acids that encode them are known in the art and can be obtained, for example, from GenBank.

In one embodiment, the methods of the present invention comprise the step of administering a composition comprising an IGF2, alone or in a composition with one or more additional compounds. IGF2 refers to GRDF, IGF-II, PP9974, C11orf43, insulin like growth factor 2. Amino acid sequences for IGF2 and nucleic acids that encode them are known in the art and can be obtained, for example, from GenBank.

In one embodiment, the methods of the present invention comprise the step of administering a composition comprising a SERPINF1 polypeptide, alone or in a composition with one or more additional compounds. SERPINF1 refers to O16, O112, PEDF, EPC-1, PIG35, serpin family F member 1. Amino acid sequences for SERPINF1 and nucleic acids that encode them are known in the art and can be obtained, for example, from GenBank.

In one embodiment, the methods of the present invention comprise the step of administering a composition comprising an IGFBP2 polypeptide, alone or in a composition with one or more additional compounds. IGFBP2 refers to IBP2, IGF-BP53, insulin like growth factor binding protein 2. Amino acid sequences for IGFBP2 and nucleic acids that encode them are known in the art and can be obtained, for example, from GenBank.

In one embodiment, the methods of the present invention comprise the step of administering a composition comprising an IGFBP6 polypeptide, alone or in a composition with one or more additional compounds. IGFBP6 refers to IBP6, insulin like growth factor binding protein 6. Amino acid sequences for IGFBP6 and nucleic acids that encode them are known in the art and can be obtained, for example, from GenBank.

In one embodiment, the methods of the present invention comprise the step of administering a composition comprising a WNT5B polypeptide, alone or in a composition with one or more additional compounds. WNT5B refers to Wnt family member 5B. Amino acid sequences for WNT5B and nucleic acids that encode them are known in the art and can be obtained, for example, from GenBank.

In one embodiment, the methods of the present invention comprise the step of administering a composition comprising a FGF9 polypeptide, alone or in a composition with one or more additional compounds. FGF9 refers to GAF, FGF-9, SYNS3, HBFG-9, HBGF-9. Amino acid sequences for FGF9 and nucleic acids that encode them are known in the art and can be obtained, for example, from GenBank.

In one embodiment, the methods of the present invention comprise the step of administering a composition comprising a FGF11 polypeptide, alone or in a composition with one or more additional compounds. FGF11 refers to FHF3, FHF-3, FGF-11, fibroblast growth factor 11. Amino acid sequences for FGF11 and nucleic acids that encode them are known in the art and can be obtained, for example, from GenBank.

In one embodiment, the methods of the present invention comprise the step of administering a composition comprising a FGF14 polypeptide, alone or in a composition with one or more additional compounds. FGF14 refers to FHF4, FHF-4, SCA27, FGF-14, fibroblast growth factor 14. Amino acid sequences for FGF14 and nucleic acids that encode them are to known in the art and can be obtained, for example, from GenBank.

In one embodiment, the methods of the present invention comprise the step of administering a composition comprising a FGFR2 polypeptide, alone or in a composition with one or more additional compounds. FGFR2 refers to BEK, JWS, BBDS, CEK3, CFDI, ECT1, KGFR, TK14, TK25, BFR-1, CD332, K-SAM, fibroblast growth factor receptor 2, Amino acid sequences for FGFR2 and nucleic acids that encode them are known in the art and can be obtained, for example, from GenBank.

In one embodiment, the methods of the present invention comprise the step of administering a composition comprising a FGFR4 polypeptide, alone or in a composition with one or more additional compounds. FGFR4 refers to TKF, JTK2, CD334, fibroblast growth factor receptor 4. Amino acid sequences for FGFR4 and nucleic acids that encode them are known in the art and can be obtained, for example, from GenBank.

In one embodiment, the methods of the present invention comprise the step of administering a composition comprising a FGF10 polypeptide, alone or in a composition with one or more additional compounds. FGF10 refers to fibroblast growth factor 10. Amino acid sequences for FGF10 and nucleic acids that encode them are known in the art and can be obtained, for example, from GenBank.

In one embodiment, the methods of the present invention comprise the step of administering a composition comprising a FGFBP1 polypeptide, alone or in a composition with one or more additional compounds. FGFBP1 refers to FGFBP, HBP17, FGF-BP, FGF-BPI, FGFBP-1, fibroblast growth factor binding protein 1. Amino acid sequences for FGFBP1 and nucleic acids that encode them are known in the art and can be obtained, for example, from GenBank.

In one embodiment, the methods of the present invention comprise the step of administering a composition comprising a DKK2 polypeptide, alone or in a composition with one or more additional compounds. DKK2 refers to DKK-2, dickkopf WNT signaling pathway inhibitor 2. Amino acid sequences for DKK2 and nucleic acids that encode them are known in the art and can be obtained, for example, from GenBank.

In one embodiment, the methods of the present invention comprise the step of administering a composition comprising an ACVR1 polypeptide, alone or in a composition with one or more additional compounds. ACVR1 refers to FOP, ALK2, SKR1, TSR1, ACTRI, ACVR1A, ACVRLK2, activin A receptor type 1. Amino acid sequences for ACVR1 and nucleic acids that encode them are known in the art and can be obtained, for example, from GenBank.

In one embodiment, the methods of the present invention comprise the step of to administering a composition comprising a SHH polypeptide, alone or in a composition with one or more additional compounds SHH refers to TPT, HHG1, HLP3, HPE3, SMMCI, TPTPS, MCOPCB5, sonic hedgehog. Amino acid sequences for SHH and nucleic acids that encode them are known in the art and can be obtained, for example, from GenBank.

In one embodiment, the methods of the present invention comprise the step of administering a composition comprising an IHH polypeptide, alone or in a composition with one or more additional compounds. IHH refers to BDA1, HHG2, indian hedgehog. Amino acid sequences for IHH and nucleic acids that encode them are known in the art and can be obtained, for example, from GenBank.

In one embodiment, the methods of the present invention comprise the step of administering a composition comprising a DHH polypeptide, alone or in a composition with one or more additional compounds. DHH refers to GDXYM, HHG-3, SRXY7, desert hedgehog. Amino acid sequences for DHH and nucleic acids that encode them are known in the art and can be obtained, for example, from GenBank.

As used herein, the terms "selectively recognizes,", "selectively binds" or "selectively recognized" mean that binding of the polypeptide, ligand or other molecule to a target or receptor is at least 2-fold greater, preferably 2-5 fold greater, and most preferably more than 5-fold greater than the binding of the molecule to an unrelated target or than the binding of another molecule to the target, as determined by techniques known in the art and described herein, such as, for example, ELISA or cold displacement assays.

As used herein, the terms "binds" or "binding" or grammatical equivalents, refer to compositions having affinity for each other. "Specific binding" is where the binding is selective between two molecules. A particular example of specific binding is that which occurs between a ligand and a receptor. Typically, specific binding can be distinguished from non-specific when the dissociation constant ($K_D$) is less than about $1 \times 10^{-5}$ M or less than about $1 \times 10^{-6}$ M or $1 \times 10^{-7}$ M. Specific binding can be detected, for example, by ELISA, immunoprecipitation, coprecipitation, with or without chemical crosslinking, two-hybrid assays and the like. Appropriate controls can be used to distinguish between "specific" and "non-specific" binding.

In one embodiment, the polypeptide, ligand or other molecule binds its target with a $K_D$ of 0.1 nM-10 mM. In one embodiment, the antibody or antigen-binding fragment binds its target with a $K_D$ of 0.1 nM-1 mM. In one embodiment, the polypeptide, ligand or other molecule binds its target with a $K_D$ within the 0.1 nM range. In one embodiment, the polypeptide, ligand or other molecule binds its target with a $K_D$ of 0.1-2 nM. In another embodiment, the polypeptide, ligand or other molecule binds its target with a $K_D$ of 0.1-1 nM. In another embodiment, the polypeptide, ligand or other molecule binds its target with a $K_D$ of 0.05-1 nM. In another embodiment, the polypeptide, ligand or other molecule binds its target with a $K_D$ of 0.1-0.5 nM. In another embodiment, the polypeptide, ligand or other molecule binds its target with a $K_D$ of 0.1-0.2 nM.

It is to be understood recombinant DNA or recombinant protein technology may be used to arrive at the polypeptides or ligands provided herein. It is further to be understood that "recombinant DNA" encompasses a DNA molecule that is comprised of segments of DNA joined together by means of molecular biology techniques. Similarly, "recombinant protein" encompasses a protein molecule that is expressed from recombinant DNA.

Where fusion proteins are used, it is to be understood that a "fusion protein" may encompass a protein formed by expression of a hybrid gene made by combining two gene sequences. Typically this is accomplished by cloning a cDNA into an expression vector in frame with an existing gene. The fusion partner may act as a reporter (e.g., β-gal) or may provide a tool for isolation purposes (e.g., GST).

Suitable systems for production of recombinant proteins include but are not limited to prokaryotic (e.g., *Escherichia coli*), yeast (e.g., *Saccharomyces cerevisiae*), insect (e.g., baculovirus), mammalian (e.g., Chinese hamster ovary), plant (e.g., safflower), and cell-free systems (e.g., rabbit reticulocyte).

The term "coding region" refers to nucleotide sequences that encode the amino acid sequences found in the nascent polypeptide as a result of translation of an mRNA molecule. The coding region is bounded in eukaryotes, on the 5' side by the nucleotide triplet "ATG" that encodes the initiator methionine and on the 3' side by one of the three triplets which specify stop codons (i.e., TAA, TAG, and TGA).

It will be appreciated that the term "amino acid sequence" and like terms, such as "polypeptide" or "protein," are not meant to limit the amino acid sequence to the complete, native amino acid sequence associated with the recited protein molecule. The term "wild-type" can encompass a gene or gene product that has the characteristics of that gene or gene product when isolated from a naturally occurring source. A wild-type gene is that which is most frequently observed in a population and is thus arbitrarily designated the "normal" or "wild-type" form of the gene.

In contrast, as a skilled artisan will appreciate, the terms "modified," "mutant," and "variant" can encompass a gene or gene product that displays modifications in sequence and/or functional properties (i.e., altered characteristics) when compared to the wild-type gene or gene product. It is noted that naturally occurring mutants can be isolated; these are identified by the fact that they have altered characteristics when compared to the wild-type gene or gene product.

It is to be understood that the term "conservative substitution" encompasses a change to that takes place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., *Biochemistry*, pg. 17-21, 2nd ed, WH Freeman and Co. [1981]). Whether a change in the amino acid sequence of a peptide results in a functional homolog can be readily determined by assessing the ability of the variant peptide to function in a fashion similar to the wild-type protein. Peptides having more than one replacement can readily be tested in the same manner. In contrast, the term "nonconservative substitution" encompasses a change in which an amino acid from one family is replaced with an amino acid from another family (e.g., replacement of a glycine with a tryptophan). Guidance in determining which amino acid residues can be substituted, inserted, or deleted without abolishing biological activity can be found using computer programs (e.g., LASERGENE software, DNASTAR Inc., Madison, Wis.).

In some embodiments, recombinant protein techniques are used to generate the polypeptides used in the compositions and methods herein. For example, recombinant techniques are described by Bitter et al., (1987) Methods in Enzymol. 153:516, Studier et al., (1990) Methods in Enzymol. 185:60, Brisson et al., (1984) Nature 310:511, Takamatsu et al., (1987) EMBO J. 6:307, Coruzzi et al., (1984) EMBO J. 3:1671 and Brogli et al., (1984) Science 224:838, Gurley et al., (1986) Mol. Cell. Biol. 6:559 and Weissbach & Weissbach, 1988, Methods for Plant Molecular Biology, Academic Press, NY, Section VIII, pp 421.

Polynucleotides described herein may be prepared using PCR techniques available in the art, or another method or procedure known to one skilled in the art. For example, the procedure involves the ligation of two different DNA sequences (See, for example, "Current Protocols in Molecular Biology", eds. Ausubel et al., John Wiley & Sons, 1992).

Plasmids are well known in the art may be employed to arrive at the compositions described herein. It will be well appreciated to the skilled artisan that a "plasmid" encompasses a small, independently replicating, piece of DNA. Similarly, a "naked plasmid" encompasses to plasmid DNA devoid of extraneous material typically used to affect transfection. The term "naked plasmid" also encompasses a plasmid that is substantially free of calcium-phosphate, DEAE-dextran, liposomes, and/or polyamines.

In some embodiments, a variety of prokaryotic or eukaryotic cells can be used as host-expression systems to express the compositions described herein. In some embodiments, these include, but are not limited to, microorganisms, such as bacteria transformed with a recombinant bacteriophage DNA, plasmid DNA or cosmid DNA expression vector containing a polypeptide coding sequence; yeast transformed with recombinant yeast expression vectors containing a polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing a polypeptide coding sequence.

In some embodiments, methods of purifying a composition described herein are employed for use in the methods provided herein. It will be appreciated to the skilled artisan that the terms "purified," "purifying", and grammatical equivalents thereof, can encompass molecules (polynucleotides or polypeptides) that are removed from their natural environment, isolated or separated. It will also be appreciated to the skilled artisan that the term "substantially purified" molecules can be at least 50% free, preferably at least 75% free, and more preferably at least 90% free from other components with which they are naturally associated.

It is to be understood that the term "wound" may encompass a disruption of the normal continuity of structures caused by a physical (e.g., mechanical) force, a biological (e.g., thermic or actinic) force, or a chemical means. In particular, the term "wound" encompasses wounds of the skin. The term "wound" may also encompass lesions, contused wounds, as well as incised, stab, lacerated, open, penetrating, puncture, abrasions, grazes, burns, frostbites, corrosions, wounds caused by ripping, scratching, pressure, and biting, and other types of wounds. The term may encompasses ulcerations (i.e., ulcers), such as ulcers of the skin. The term "wound" may also encompass a healing cutaneous wound.

It is to be understood that the term "wound healing" can encompass a regenerative process with the induction of a temporal and spatial healing program comprising wound closure and the processes involved in wound closure. The term "wound healing" can also encompass the processes of granulation, neovascularization, fibroblast, endothelial and epithelial cell migration, extracellular matrix deposition, re-epithelialization, and remodeling.

It will be appreciated by a skilled artisan that the term "wound closure" can encompass healing of a wound wherein sides of the wound are rejoined to form a continuous barrier (e.g., intact skin). In another embodiment, the compositions and methods provided herein promote tissue regeneration. In another embodiment, the compositions and methods provided herein limit scarring of tissues such as glia, tendons, eye tissue, ligament or skin.

It will be appreciated that "granulation" encompasses the process whereby small, red, grainlike prominences form on a raw surface (that of wounds or ulcers) as healing agents. It also will be appreciated that "neovascularization" encompasses the new growth of blood vessels with the result that the oxygen and nutrient supply is improved. Similarly, it will be appreciated that "angiogenesis" encompasses the vascularization process involving the development of new capillary blood vessels. It will also be appreciated that "cell migration" refers to the movement of cells (e.g., fibroblast, endothelial, epithelial, etc.) to the wound site.

It is to be understood that "extracellular matrix deposition" can encompass the secretion by cells of fibrous elements (e.g., collagen, elastin, reticulin), link proteins (e.g., fibronectin, laminin), and space filling molecules (e.g., glycosaminoglycans). It will be appreciated that "type I collagen" encompasses the most abundant collagen, which forms large well-organized fibrils having high tensile strength. It will be appreciated that "re-epithelialization" encompasses the reformation of epithelium over a denuded surface (e.g., wound). It will also be appreciated that "remodeling" encompasses the replacement of and/or devascularization of granulation tissue.

It will be appreciated that "impaired healing capabilities" encompass wounds that are characterized by a disturbed wound healing process. Examples of wounds with impaired healing capabilities are wounds of diabetic patients and alcoholics, wounds which are infected by microorganisms, ischemic wounds, wounds of patients suffering from deficient blood supply or venous stasis, and ulcers. It will also be appreciated that a "chronic wound" encompasses a wound that does not fully heal even after a prolonged period of time (e.g., 2 to 3 months or longer).

In one embodiment, the compositions and methods of the present invention promote skin regeneration. In another embodiment, the compositions and methods of the present invention improve the cosmetic appearance of a wound or scar, for example, a closer color match with surrounding skin.

It will be understood that the terms "administering," "administration," and like terms encompass any suitable method which, in sound medical or cosmetic practice, delivers a composition to a subject in such a manner as to provide a positive effect on a dermatological wound, disorder, condition, or appearance. The compositions are preferably administered such that they cover the entire area to be treated. It will be further understood that "direct to administration" encompasses a method which, in sound medical or cosmetic practice, delivers a composition to a subject without the use of another composition, delivery agent, or device. "Indirect administration" encompasses a method which, in sound medical or cosmetic practice, delivers a composition to a subject with the use of another composition, delivery agent, or device.

"Administration" to a subject is not limited to any particular delivery system and may include, without limitation, topical, intralesional, intradermal, subepidermal transdermal, oral (for example, in capsules, suspensions or tablets), parenteral (including subcutaneous, intradermal, subepidermal, intravenous, intramedullary, intraarticular, intramuscular, or intraperitoneal injection), or rectal. Administration to a subject may occur in a single dose or in repeat administrations, and in a variety of physiologically acceptable salt forms, and/or with an acceptable pharmaceutical carrier and/or additive as part of a pharmaceutical composition. Physiologically acceptable salt forms and standard pharmaceutical formulation techniques are well known to persons skilled in the art (see, e.g., Remington's Pharmaceutical Sciences, Mack Publishing Co.).

In one example, a single bolus is administered. In another example, several divided doses are administered over time. In yet another example, a dose may be proportionally reduced or increased as indicated by the exigencies of the therapeutic situation. Dosage unit form, as used herein, refers to physically discrete units suited as unitary dosages for treating a subject. Each unit contains a predetermined quantity of an active agent calculated to produce a desired therapeutic effect. In some embodiments, the dosage unit forms of the invention are dependent on the characteristics of the active agent and the particular therapeutic or prophylactic effect to be achieved.

The compositions described herein may be administered only once or it multiple times. For multiple dosages, the composition may be, for example, administered three times a day, twice a day, once a day, once every two days, twice a week, weekly, once every two weeks, or monthly.

It is to be noted that dosages may vary with the type and severity of the condition to be alleviated. It is further understood that for a particular subject, specific dosage regimens should be adjusted over time according to the individual need and the professional judgment of the person administering or supervising the administration of the compositions.

It is to be understood that the terms an "effective amount" or a "therapeutically effective amount" of a composition, an active agent, an ingredient, or pharmaceutically active agent or ingredient can encompass an amount of the composition or pharmaceutically active agent sufficient to have a positive effect on the affected area. Accordingly, these amounts are sufficient to positively modify the skin wound, disorder, condition, or appearance to be treated but low enough to avoid serious side effects, within the scope of sound medical or dermatological advice. When used to treat a dermatological condition or disorder, effective amounts of the pharmaceutically active agent will vary with the particular condition or conditions being treated, the severity of the condition, the duration of the treatment, the specific components of the composition being used, and like factors. It is to be understood that the term "extended period of time" can encompass the shelf life of the compositions provided herein, including time spent on the shelf at a pharmacy as well as the entire time period after sale of the compositions during which the compositions remains effective for the indicated use. As used herein, the phrase a "label claim" refers to statements made on a label or literature accompanying a pharmaceutical product for sale. In this regard, the phrase "label claim" is intended to include indications on the label, packaging, and or literature of a pharmaceutical product of the amount(s) of any active ingredient(s) present in that product.

As used herein, the phrase "pharmaceutically acceptable" refers to those compounds, materials, compositions, carriers, and/or dosage forms which are, within the scope of sound medical judgment, suitable for use in contact with the tissues of human beings or animals without excessive toxicity, irritation, allergic response, or other problem or complication, commensurate with a reasonable benefit/risk ratio.

The term "pharmaceutically acceptable salts" encompasses salts of the active agent(s) which possess the same pharmacological activity as the active compound(s) and which are neither biologically nor otherwise undesirable. A salt can be formed with, for example, organic or inorganic acids. Non-limiting examples of suitable acids include acetic acid, acetylsalicylic acid, adipic acid, alginic acid, ascorbic acid, aspartic acid, benzoic acid, benzenesulfonic acid, bisulfic acid, boric acid, butyric acid, camphoric acid, camphorsulfonic acid, carbonic acid, citric acid, cyclopentanepropionic acid, digluoonic acid, dodecylsulfic acid, ethanesulfonic acid, formic acid, fumaric acid, glyceric acid, glycerophosphoric acid, glycine, glucoheptanoic acid, gluconic acid, glutamic acid, glutaric acid, glycolic acid, hemisulfic acid, heptanoic acid, hexanoic acid, hippuric acid, hydrobromic acid, hydrochloric acid, hydroiodic acid, hydroxyethanesulfonic acid, lactic acid, maleic acid, malic acid, malonic acid, mandelic acid, methanesulfonic acid, mucic acid, naphthylanesulfonic acid, naphthylic acid, nicotinic acid, nitrous acid, oxalic acid, pelargonic, phosphoric acid, propionic acid, saccharin, salicylic acid, sorbic acid, succinic acid, sulfuric acid, tartaric acid, thiocyanic acid, thioglycolic acid, thiosulfuric acid, tosylia acid, undecylenic acid, naturally and synthetically derived amino acids. Non-limniting examples of base salts include ammonium salts;

alkali metal salts, such as to sodium and potassium salts; alkaline earth metal salts, such as calcium and magnesium salts; salts with organic bases, such as dicyclohexylamine salts; methyl-D-glucamine; and salts with amino acids, such as arginine, lysine, and so forth. Also, the basic nitrogen-containing groups can be quaternized with such agents as lower alkyl halides, such as methyl, ethyl, propyl, and butyl chlorides, bromides, and iodides; dialkyl sulfates, such as dimethyl, diethyl, dibutyl, and diamyl sulfates; long chain halides, such as decyl, lauryl, myristyl, and stearyl chlorides, bromides, and iodides; asthma halides, such as benzyl and phenethyl bromides; and others. Water or oil-soluble or dispersible products are thereby obtained.

It is to be understood that the term "sensitivity" may encompass the degree of skin irritation or skin inflammation, as exemplified by parameters in suitable assays for measuring sensitivity, inflammation, irritation, and the like. One such assay is the Jordan-King assay.

It is to be understood that the terms "storage stable" or "storage-stable" encompass the ability compositions to have a long shelf life, including time spent on the shelf at a pharmacy, as well as the time period after sale of the composition, during which time the composition maintains its effectiveness and pharmaceutically acceptable appearance. Accordingly, compositions are stable in that they exhibit a minimum amount of degradation during an extended period of storage.

Pharmaceutically acceptable carriers" include any excipient which is nontoxic to the cell or subject being exposed thereto at the dosages and concentrations employed. Pharmaceutical compositions may also include one or more additional therapeutic agents. Pharmaceutically acceptable carriers include solvents, dispersion media, buffers, coatings, antibacterial and antifungal agents, wetting agents, preservatives, buggers, chelating agents, antioxidants, isotonic agents and absorption delaying agents. Pharmaceutically acceptable carriers include water; saline; phosphate buffered saline; dextrose; glycerol; alcohols such as ethanol and isopropanol; phosphate, citrate and other organic acids; ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; EDTA; salt forming counterions such as sodium; and/or nonionic surfactants such as TWEEN, polyethylene glycol (PEG), and PLURONICS; isotonic agents such as sugars, polyalcohols such as mannitol and sorbitol, and sodium chloride; as well as combinations thereof. Antibacterial and antifungal agents include parabens, chlorobutanol, phenol, ascorbic acid, and thimerosal.

In another embodiment, the present compositions may be used in combination with an additional pharmaceutical dosage form to enhance their effectiveness in treating a skin disease, disorder, or condition. In this regard, the present compositions may be administered as part of a regimen additionally including another pharmaceutical, and/or pharmaceutical dosage form known in the art as effective for the treatment of a skin disorder. Accordingly, the additional active ingredient or additional pharmaceutical dosage form can be applied to a patient either directly or indirectly, and concomitantly or sequentially, with the compositions described herein. In some embodiments, the present compositions may be administered as part of a regimen further comprising administering, for example by intralesional injection, a corticosteroid, such as cortisone, to the subject.

The pharmaceutical compositions provided herein may be formulated in a variety of ways, including for example, solid, semi-solid (e.g., cream, ointment, and gel), and liquid dosage forms, such as liquid solutions (e.g., topical lotion or spray), dispersions or suspensions, tablets, pills, powders, liposomes and suppositories. In some embodiments, the compositions are in the form of injectable or infusible solutions. The compositions may be in a form suitable for oral, intradermal intradermal, subepidermal, intravenous, intraarterial, intramuscular, subcutaneous, parenteral, transmucosal, transdermal, intralesional, or topical administration. Preferably, compositions are formulated for injection or for oral or topical administration. The composition may be formulated as an immediate, controlled, extended or delayed release composition.

More particularly, pharmaceutical compositions suitable for use include sterile aqueous solutions (where water soluble) or dispersions and sterile powders for the extemporaneous preparation of sterile solutions or dispersions. They should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use are described in Remington's Pharmaceutical Sciences, Mack Publishing Co., $16^{th}$ ed. (1980).

The compositions may also include isotonic agents, for example, sugars, polyalcohols, such as mannitol, sorbitol, or sodium chloride. Prolonged absorption of injectable compositions can be brought about by including in the composition an agent which delays absorption, for example, aluminum monostearate and gelatin.

Sterile solutions can be prepared by incorporating the agent, by itself or in to combination with other active agents, in the required amount in an appropriate solvent with one or a combination of ingredients enumerated herein, as desired, followed by filtered sterilization. Generally, dispersions are prepared by incorporating the active agent into a sterile vehicle, which contains a basic dispersion medium and the required other ingredients from those enumerated above. In the case of sterile powders for the preparation of sterile injectable solutions, one method of preparation is vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit. Such articles of manufacture will preferably have labels or package inserts indicating that the associated compositions are useful for treating a subject suffering from, or predisposed to androgenetic alopecia, baldness or hair loss.

Effective doses of the compositions described herein, for the methods described herein vary depending upon many different factors, including the specific agent used, the sensitivity of the subject for that agent, means of administration, target site, physiological state of the patient, whether the patient is human or an animal, other medications administered, and whether treatment is prophylactic or therapeutic.

Usually, the patient is a human but non-human mammals including transgenic mammals can also be treated. Treatment dosages may be titrated using routine methods known to those of skill in the art to optimize safety and efficacy.

Further provided herein are kits comprising a therapeutically effective amount of a DP-2 antagoan agent described herein.

As used herein, the term, "selective" with respect to inhibition or stimulation means preferential inhibition or stimulation, respectively, of a first activity relative to a second activity (e.g., preferential inhibition of one pathway to another pathway; preferential inhibition relative to other receptors; or preferential inhibition of a mutant to a wild-type or vice versa). In some embodiments, the agent is greater than five times more selective, greater than ten times more selective, greater than fifty times more selective, greater than 100 times more selective, or greater than 1000 times more selective for the desired molecular target or pathway versus an undesired molecular target or pathway. In some embodiments, an antagonist or agonist will inhibit or stimulate, respectively, the first activity of the molecular target or pathway by at least 2-fold, at least 5-fold, at least 10-fold, at least 20-fold, at least 50-fold, at least 100-fold relative to the second activity under the same conditions. The activity of a molecular target or pathway may be measured by any reproducible means and may be measured in vitro or in vivo.

As used herein, "modulating" refers to "stimulating" or "inhibiting" an activity to of a molecular target or pathway. For example, a composition modulates the activity of a molecular target or pathway if it stimulates or inhibits the activity of the molecular target or pathway by at least 10%, by at least about 20%, by at least about 25%, by at least about 30%, by at least about 40%, by at least about 50%, by at least about 60%, by at least about 70%, by at least about 75%, by at least about 80%, by at least about 90%, by at least about 95%, by at least about 98%, or by about 99% or more relative to the activity of the molecular target or pathway under the same conditions but lacking only the presence of the composition. In another example, a composition modulates the activity of a molecular target or pathway if it stimulates or inhibits the activity of the molecular target or pathway by at least 2-fold, at least 5-fold, at least 10-fold, at least 20-fold, at least 50-fold, at least 100-fold relative to the activity of the molecular target or pathway under the same conditions but lacking only the presence of the composition. The activity of a molecular target or pathway may be measured by any reproducible means. The activity of a molecular target or pathway may be measured in vitro or in vivo by an appropriate assay known in the art. Control samples (untreated with the composition) can be assigned a relative activity value of 100%. A change in activity caused by the composition can be measured in the assays.

Various dosage ranges are contemplated and may vary based on the agent used and the sensitivity of the subject for that agent. For example, the dose of the agent is between about 0.1-1000 mg/day, about 1-1000 mg/day about 5-500 mg/day, about 10-300 mg/day, about 20-200 mg/day, about 40-150 mg/day, about 60-100 mg/day, about 0.1-100 mg/day, about 0.1-50 mg/day, about 0.1-20 mg/day, about 0.1-10 mg/day, about 0.1-5 mg/day, or about 0.5-5 mg/day.

As used herein, the terms "treat" and "treatment" refer to therapeutic treatment, including prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), a reduction in the severity thereof, delay, inhibit or slow the progression of a disease or condition, amelioration or palliation of the disease or condition, and remission (whether partial or total) of the disease or condition. "Treatment" can also mean prolonging survival as compared to expected survival if not receiving treatment. Those in need of treatment include those already with the disease or condition as well as those prone to having the disease or condition or those in which the disease or condition is to be prevented. Treatment need not mean that the wound, disease, disorder, or condition is totally cured. A useful composition herein needs only to reduce the severity of a skin wound, disease, disorder, or to condition, reduce the severity of symptoms associated therewith, provide improvement to a patient's quality of life, or delay, prevent, or inhibit the onset of a skin disease, disorder, or condition.

In some embodiments, a protein or polypeptide provided herein comprises a modification. It is to be understood by a skilled artisan that the modification can be a modification known in the art to impart a functional property that would not otherwise be present if it were not for the presence of the modification. Encompassed are proteins which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH4, acetylation, formylation, oxidation, reduction, metabolic synthesis in the presence of tunicamycin, etc.

It will be appreciated that the term "modification" can encompass an amino acid modification such as an amino acid substitution, insertion, and/or deletion in a polypeptide sequence.

The term "subject" refers to a mammal including a human in need of therapy for, or susceptible to, a condition or its sequelae. The subject may include dogs, cats, pigs, cows, sheep, goats, horses, rats, and mice and humans. The term "subject" does not exclude an individual that is normal in all respects.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, when referring to a measurable value such as an amount, a temporal duration, a concentration, and the like, may encompass variations of ±20% or ±10%, more preferably ±5%, even more preferably ±1%, and still more preferably ±0.1% from the specified value, as such variations are appropriate to perform the disclosed methods.

The following examples are presented in order to more fully illustrate the preferred embodiments of the invention. They should in no way be construed, however, as limiting the broad scope of the invention.

EXAMPLES

Example 1: Materials and Methods

Wounding Experiments.

All animal experiments were carried out in accordance to with the guidelines of the IACUC of the University of Pennsylvania and the University of California, Irvine. Full thickness 1.5×1.5 cm (2.25 cm$^2$) excisional wounds were inflicted on the backs of three to eight week-old mice as described in M. Ito et al., Nature 447:316 (2007).

Phenotype Quantification Methodology.

Whole mount wounds were stained for Oil Red O and the number of regenerated hair follicles was counted from the skin surface, where each new hair is clearly visible. The number of new adipocytes was counted from the underside, where each adipocyte is clearly visible due to their very large size and prominent marking by Oil Red O dye. For each experiment, adipose tissue regeneration was quantified as the ratio of all new adipocytes/all new hair follicles (aka adipocyte/hair follicle index). The index values for all experiments, statistical significance and number of biological replicates are summarized in Table 1 below. Some wound samples (FIG. 2B) were stained for lacZ and photographed, then additionally stained for Oil Red O and photographed again. Adipocytes were then micro-dissected and photographed under stereomicroscope.

TABLE 1

Mice used in the Examples.

| Transgenic mouse line | Adipocyte/ hair index | P value | Post-wounding day | N |
|---|---|---|---|---|
| Experiment: Constitutive deletion of Ppary in myofibroblasts | | | | |
| SM22-Cre; Ppary$^{flox/flox}$ (mutant) | 0.62 ± 0.2 | P < 0.05 | Day 28 | 7 |
| SM22-Cre; Ppary$^{flox/+}$ (control) | 24.1 ± 6.8 | | Day 28 | 7 |
| Experiment: Inducible deletion of Ppary in myofibroblasts | | | | |
| SMA-CreERT2; Ppary$^{flox/flox}$ (mutant) | 0.5 ± 0.07 | P < 0.05 | Day 28 | 6 |
| SMA-CreERT2; Ppary$^{flox/+}$ (control) | 22.7 ± 5.1 | | Day 28 | 6 |
| Experiment: Whole-body deletion of Zfp423 | | | | |
| Zfp423−/− (mutant) | 0.07 ± 0.06 | P < 0.05 | Day 28 | 9 |
| Zfp423+/− (control) | 29.6 ± 5.4 | | Day 28 | 9 |
| Experiment: Skin specific over-expression of soluble BMP antagonist Noggin | | | | |
| K14-Noggin (mutant) | 0.2 ± 0.1 | P < 0.05 | Day 28 | 10 |
| WT (control) | 30.6 ± 6.3 | | Day 28 | 10 |
| Experiment: Inducible deletion of BMP receptor Bmpr1a in Myofibroblasts | | | | |
| SMA-CreERT2; Bmpr1a$^{flox/flox}$ (mutant) | 0.38 ± 0.36 | P < 0.05 | Day 28 | 6 |
| Tamoxifen treated control | 23.9 ± 1.5 | | Day 28 | 3 |
| Experiment: Pharmacological treatment of mice with LDN-193189 | | | | |
| WT (treated) | 0.58 ± 0.35 | P < 0.05 | Day 28 | 7 |
| WT (vehicle control) | 5.8 ± 1.4 | | Day 28 | 4 |
| Experiment: Skin specific over-expression of soluble WNT ligand Wnt7a | | | | |
| K14-Wnt7a (mutant) | 0.6 ± 0.3 | P < 0.05 | Day 28 | 6 |
| WT (control) | 28 ± 4.2 | | Day 28 | 6 |

Human Scar Cell Isolation and Culture.

All human experiments were carried out in accordance with the guidelines of the IRB of the University of California, Irvine, Children's Hospital Los Angeles and Kyungpook National University. Keloid fibroblasts were isolated as described in Y. S. Lee et al., Wound repair and regeneration: official publication of the Wound Healing Society [and] the European Tissue Repair Society 24:302 (2016). Human hypertrophic scar myofibroblasts were derived from clinical specimen biopsies and expanded in vitro as described in M. Vangipuram et al., Journal of visualized experiments: JoVE, e3779 (2013). Information pertinent to human scars is listed in Table 2.

TABLE 2

Primary human cells used in the Examples.

| ID | Gender | Ethnicity | Age (yrs.) | Source | Clinical History |
|---|---|---|---|---|---|
| Wound healing pathology: Keloid scar | | | | | |
| K126 | Female | Caucasian | 62 | Breast | NA |
| K117 | Female | Caucasian | 30 | NA | NA |
| K120 | Female | A. American | NA | NA | NA |
| Wound healing pathology: Hypertrophic scar | | | | | |
| HS-1 | Female | Caucasian | 60 | Breast | NA |
| HS-2 | Female | Caucasian | 62 | Breast | Breast cancer |
| HS-3 | Female | Asian | 50 | Breast | Breast cancer |

Primary Mouse Adipogenic Cell Culture.

Primary scar cells were isolated from day 15 wounds as described in D. Gay et al., Nature medicine 19:916 (2013) with minor modifications. Single cell fractions were created and cultured to confluence in high-glucose to DMEM (Gibco) supplemented with 10% FBS (Atlanta Biologicals) and 10,000 μl/ml Pen/Strep cocktail (Gibco). Upon confluency, cells were cultured in adipocyte differentiation media alone (Cell Solutions) or DMEM supplemented with 5 μg/ml insulin (Sigma), and 1 μM rosiglitazone (Sigma) with either 6 ng/ml of recombinant hBMP4 (R&D Systems), or 25 ng/ml of recombinant hBMP2 (R&D Systems), or differentiation media alone (Cell Solutions). After three days, cells differentiation media was switched to adipocyte maintenance media (Cell Solutions). Cells were cultured in a water-jacketed incubator at 37° C. with 5% $CO_2$ output Primary Human Adipogenic Cell Culture.

Primary human scar cells were cultured in DMEM/F12 media (Gibco) supplemented with 10% FBS (Fisher Scientific). Upon confluency, cells were switched to serum free DMEM/F12 media and treated with 20 ng/ml recombinant hBMP4 protein (R&D Systems) for 48 hours before differentiation. For the hair follicle co-culture, cells were grown in 12-well trans-well plates. Once near confluency, medium was changed to William's E hair follicle organ culture medium, and 40 microdissected human scalp anagen hair follicles were co-cultured on top of the membrane insert in each well for 5 days. Control cells were cultured in William's E medium without hair follicles. In all cases, adipogenic differentiation was induced by adding adipogenic cocktail: DMEM/F12 media supplemented with 1% ITS premix (insulin-transferrin-selenium; BD Biosciences), 0.5 mM isobutylmethylxanthine (Sigma), 0.1 μM cortisol (Sigma), 1 μM dexamethasome (Sigma), 0.2 nM triiodothyronine (Sigma), and 1 μM rosiglitazone (Cayman Chemical). After 4 days of induction, cells were changed to maintenance media: DMEM/F12 media supplemented with 1% ITS premix (BD Biosciences), 0.1 μM cortisol (Sigma), and 0.2 nM triiodothyronine (Sigma). For the hair follicle co-culture, cells were maintained in the induction media for 7 days. Lipid droplets were visualized after 7 days and cells were harvested for RNA isolation on day 10.

Murine stromo-vascular fraction (SVF) isolation.

Visceral fat pads were dissected, minced and digested with 2.4 U/ml collagenase and 1.5 U/ml dispase mixture for 60 to minutes at 37° C. with constant agitation. Digestion was then stopped with MEM+10% FBS. Cells were washed, filtered and centrifuged. Upon centrifugation, cells separate into two layers: fat-laden adipocytes at the top and SVF pellet at the bottom. The SVF pellet was collected and used in hair patch assays.

Hair patch assay.

Epithelial and dermal cells were isolated from neonatal C57BL/6 mouse skin. $0.5 \times 10^6$ epithelial and $1 \times 10^6$ dermal cells were injected intradermally into nu/nu mice (Charles River). In some experiments, freshly isolated Retn-lacZ SVF cells were added. In other experiments neonatal dermis was substituted by $1 \times 10^6$ of Retn-lacZ DP cells that were previously expanded for two weeks. The resulting patch assays were dissected and studied 14 days later.

Histology and immunohistochemistry.

Immunostaining was performed on paraffin sections with heat-based antigen retrieval. The primary antibodies used were goat anti-Zfp423 (1:50; Abcam), rabbit anti-phospho-CEBPβ$^{T188}$ (1:50; Cell Signaling), rabbit anti-Pparγ (1:50; Cell Signaling), rabbit anti-Perilipin (1:750; Cell Signaling), rabbit anti-SMA (1:200; Abcam), mouse anti-PCNA (1:200; Abcam), rabbit anti-phospho-Smad1/5/8 (1:50, Cell Signaling), rabbit anti-keratin K5 (1:250, Abcam), mouse anti-β-galactosidase (1:300; Developmental Studies Hybridoma Bank), mouse anti-Cre Recombinase (1:1000; Millipore), rabbit anti-tdTomato (1:1000; Rockland). Antibody masking was performed with donkey anti-rabbit whole IgG at 20 ug/ml (Jackson ImmunoResearch).

qRT-PCR.

Total RNA was isolated using Trizol reagent (Thermo) or RNEasy Micro-Kit (Qiagen) as per manufacturer's protocol with minor modifications. Total RNA was reverse-transcribed and cDNA was amplified using PCR primers described in J. Ishibashi et al., Mol Cell Biol 32:2289 (2012). See Tables 3 and 4 for the sequences of primers used.

TABLE 3

Mouse primers used in the Examples.

| Gene | Forward Primer (5'-3') | Reverse Primer (5'-3') |
|---|---|---|
| Mouse | | |
| Gapdh | GAAGGTGAAGGTCGGAGT | GAAGATGGTGATGGGATTTC |
| Adipoq | GCACGGCAAGTTCTACTGCAA | GTAGGTGAAGAGAACGGCCTTGT |
| Retn | CTGTCCAGT CTA TCC TTG CAC AC | CAGAAGGCACAGCAGTCTTGA |
| Pparg | GTCCACGTTTCGATCCGTAGA | GGCCAGCATCGTCGTGTAGATGA |
| Wnt2b | AGAGTGCCAACACCAGTTCC | ACGAGGTCATTTTTCGTTGG |
| Sox9 | ACGGCTCCAGCAAGAACAAG | TTGTGCAGATGCGGGTACTG |
| Zfp423 | TGGCCTGGGATTCCTCTGT | TTGTCGCACTGTTCAGTTCTC |
| Bmp4 | GCCCTGCAGTCCTTCGCTGG | CTGACGTGCTGGCCCTGGTG |
| Lepr | ACGTGGTGAAGCATCGTACT | GGCCATGAGAAGGTAAGGTT |
| Wif1 | GATTTCAGGAAAGCCCAACAAAGAA | GTTGGATCTGCCATGATGCCTTT |
| Klf15 | CACCAAGAGCAGCCACCTCA | CGGGACACTGGTACGGCTTC |
| Id1 | CGACTACATCAGGGACCTGCA | GAACACATGCCGCCTCGG |
| Dlk1 | AAGGACTGCCAGAAAAAGGAC | GCAGAAATTGCCTGAGAAGC |

TABLE 4

Human primers used in the Examples.

| Gene | Forward Primer (5'-3') | Reverse Primer (5'-3') |
|---|---|---|
| Human | | |
| ADIPOQ | CCCAACATGCCCATTCGCTTT | ACAGCCCAGGAATGTTGCAGT |
| ADIPSIN | TGGAGGTGGGTGCTTGTAGTT | GGTGCAATCACAACTCACTGC |
| FABP4 | GTCATGAAAGGCGTCACTTCCAC | CAATGCGAACTTCAGTCCAGGTC |
| PPARG2 | GCAGGAGATCACAGAGTATGCCA | TCAAGGAGGCCAGCATTGTGT |
| RPS18 | TGCAGAATCCACGCCAGTACA | ATCTTCTTCAGTCGCTCCAGGTC |
| ZNF423 | CCAAATCCACGTTGCCAACCA | TGCTCAATGAGGTGACAGAGGAG |

Fluorescence-activated cell sorting.

Figure 16:
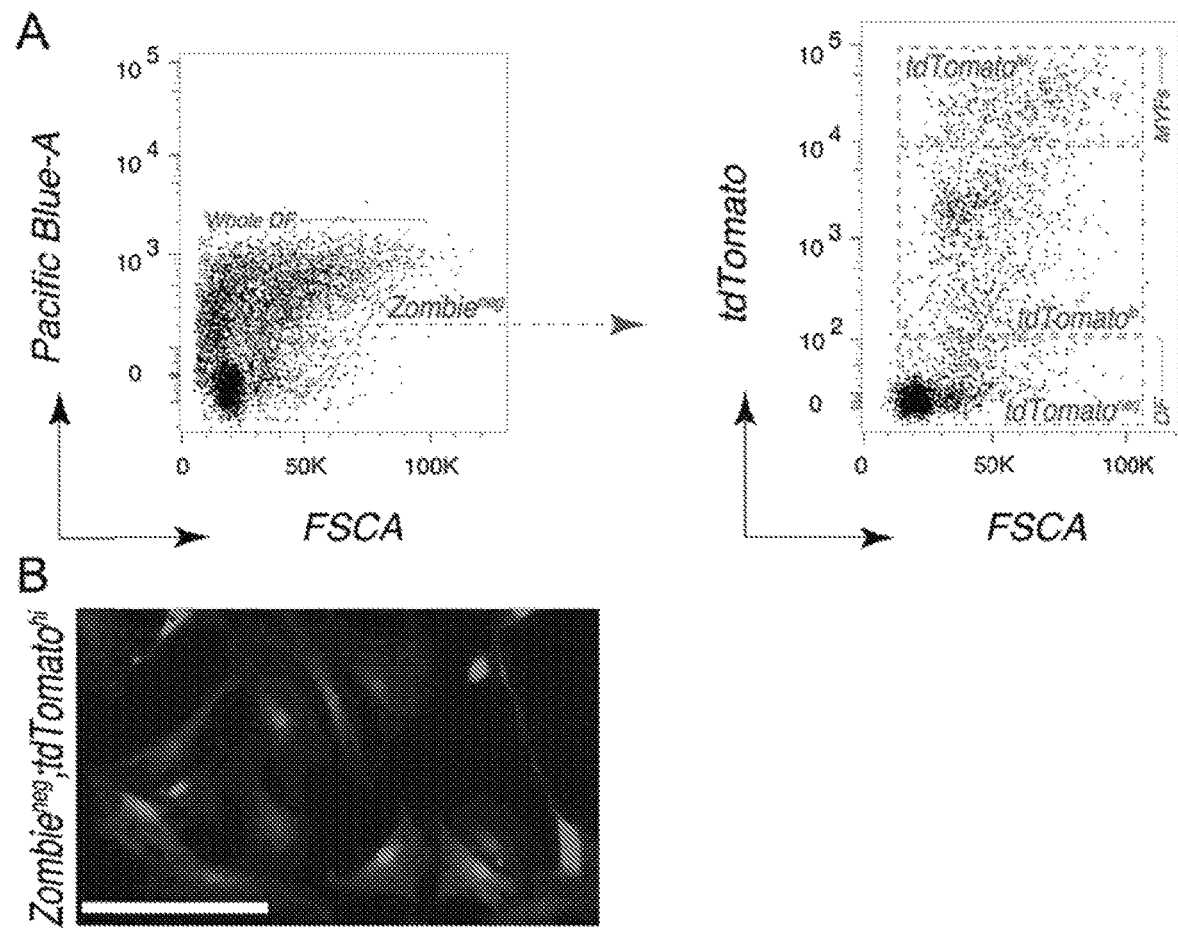
FIG. 16: Sorting strategy for wound myofibroblasts. (A) Schematic representation of sequential FACS gating of wound myofibroblasts. Single dermal fractions (DF) from Sm22-Cre;tdTomato mouse wounds were gated on viable cells (Zombie$^{neg}$). tdTomat$^+$ populations were classified as tdTomato$^{lo}$ and tdTomato$^{hi}$. (B) tdTomato$^{hi}$ cells displayed large size, prominent spindle-shaped morphology and high tdTomato expression. Size bars: B—200 µm.
Figure 17:
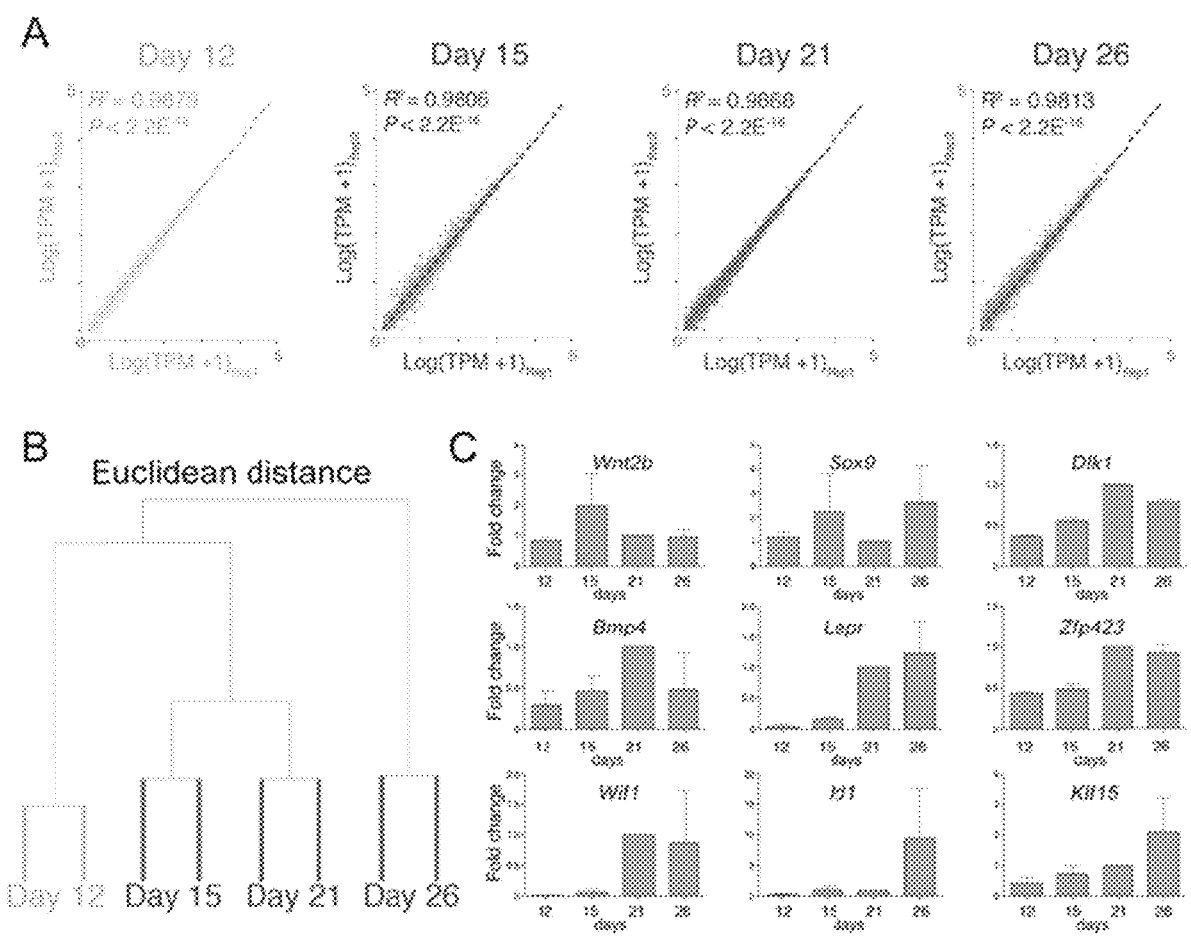
FIG. 17: Analyses of myofibroblast RNA-sequencing data during wound healing. (A) Spearman correlation coefficients for gene expression profiles of biological replicates. (B) to Hierarchical clustering of myofibroblasts based on Euclidean distance. (C) qRT-PCR against select genes in sorted cutaneous myofibroblasts at different time points post-wounding (n=2 for each time point). Data are presented as the mean of raw expression normalized to post-wounding day 21.

Dorsal skin was collected from mice at different post-wounding time points. Scar tissue was micro-dissected, devoid of fascia and incubated in Dispase II solution (Sigma) to separate epidermis from dermis. Dermis was disaggregated into single cells with Collagenase IV (Sigma) at 37° C. with constant rotation. Single cell fractions were stained with Zombie Violet™ (1:1000; BioLegend) and FACS-sorted as Zombie$^{neg}$;tdTomato$^{hi}$ using a BD FACSAria II flow cytometer (BD Biosciences) (see FIG. 16).

RNA isolation and SMART-seq2.

Sorted, uncultured Zombie$^{reg}$;tdTomato$^{hi}$ myofibroblasts were re-suspended in RLT buffer supplemented with 1% beta-mercaptoethanol and homogenized with QIAshredder (Qiagen). Total RNA was isolated using the RNEasy Micro-Kit (Qiagen) as per manufacturer's protocol with minor modifications, including DNase I treatment (Qiagen). Optimal-quality RNAs were considered for cDNA library preparation (RIN>8.8). Full-length cDNA library amplification was performed as described in S. Picelli et al., Nature methods 10:1096 (2013) and in S. Picelli et al., Nat Protoc 9:171 (2014). Briefly, 1ng total RNA was reversed-transcribed, and resulting cDNA was pre-amplified for 17 cycles. Tagmentation was carried out on 18 ng cDNA using the Nextera DNA Sample Preparation Kit (Illumina). The Tn5 tagmentation reaction was carried out at 55° C. for 5 minutes and purified using PCR Purification Kit (Qiagen). Adapter-ligated fragments were amplified using limited cycle enrichment PCR with Nextera barcodes. Libraries were amplified for 7 continuous cycles and resulting libraries were purified with AMPure XP beads (Beckman Coulter). Library quantification was done using KAPA for Illumina Sequencing Platforms (Illumina). Libraries were multiplexed and sequenced as paired-end on a Next-Seq500 Illumina platform (Cluster density=296K/mm2, Clusters PF=71.2%, Q30=87.6%).

Smart-Seq2 Analyses.

Paired-end reads were aligned to the mouse reference to genome (mm10/gencode.vM4) using bowtie (version 1.0.0) with default parameters. Transcripts were quantified using the RNA-seq by Expectation-Maximization algorithm (RSEM) (version 1.2.12) with the following default parameters: rsem-calculate-expression -p $CORES—paired-end. Samples displaying >20,000,000 mapped reads and >75% mapping efficiency were considered for downstream analyses. Differential expression dynamics across single time experimental series was identified using the two-step regression model algorithm MaSigPro with a P-value cutoff of 0.05 for multiple hypothesis testing and a false discovery control rate of 0.01. Principle component analysis was performed using the R ggbiplot package. Data is available at GEO: GSE84256 (URL: www.ncbi.nlm.nih.gov/geo/query/acc.cgi?acc=GSE84256).

Meta-analyses.

Transcriptome-wide meta-analyses was performed on microarray and RNA-seq datasets from skin-derived precursors (GEO: GSM464261), Nes-Cre$^+$ and Nes-GFP$^+$ subcutaneous fat pericytes (GEO: GSM1573101), E14.5 dermal fibroblasts (DFs) and dermal condensate cells (DCs) (GEO: GSE70288), P5 dermal fibroblasts (DFs) and dermal papilla cells (DPs) (GEO: GSE77197), P56 Engr$^+$/Engr$^{neg}$ fibroblasts (GEO: GSE65402), P2 Sca1$^+$/Sca1$^+$ fibroblasts (GEO: GSE76751) and cutaneous myofibroblasts isolated from days 12, 15, 21 and 26 post-wounding (GEO: GSE84256). Processing of RNA-seq data sets: Reads from single-end data sets and single reads (read 1) from paired-end data sets were trimmed to 43 bp. The trimmed reads were aligned to the mouse genome (mm10/gencode.vM9) using bowtie (version 1.0.0) with the following parameters: —offrate 1 -a -m 200—best -p 16—seedlen 25 -n 2 -v 2. Gene expression levels were obtained using RSEM (version 1.2.25) and used for the downstream analyses. Gene expression levels were transformed to Z-scores. Microarray data processing: All microarray data processing was performed in R (version 3.2.3) using corresponding Bioconductor packages. Raw microarray data were downloaded from GEO. Data normalization was done using the rma function of affy package. Median expression values were kept for genes that had multiple mapping probes. The gene expression levels from the microarray data sets were combined in a matrix and quantile-normalized using the normalizeQuantiles function of limma package. Gene expression levels were transformed to Z-scores. Combined RNA-seq and microarray data analyses: Gene expression Z-scores from RNA-seq and microarray data sets were combined into a matrix and batch-effect corrected using the ComBat function of sva package. Principle component analysis was performed using the R prcomp function.

Example 2: Regeneration of Fat Cells from Myofibroblasts During Wound Healing

Although regeneration via the reprogramming of one cell lineage to another occurs in fish and amphibians, it is not observed in mammals. During wound healing adipocytes to regenerate from myofibroblasts, a cell type thought to be differentiated and non-adipogenic was discovered in mouse. Myofibroblast reprogramming required neogenic hair follicles, which triggered BMP signaling and then activation of adipocyte transcription factors expressed during development. Overexpression of the BMP antagonist, noggin, in hair follicles or deletion of the BMP receptor in myofibroblasts prevented adipocyte formation. Adipocytes formed from human keloid fibroblasts when treated with either BMP or when placed with human hair follicles in vitro. Thus, the myofibroblast is identified as a plastic cell type that may be manipulated to treat scars in humans.

Figure 5:
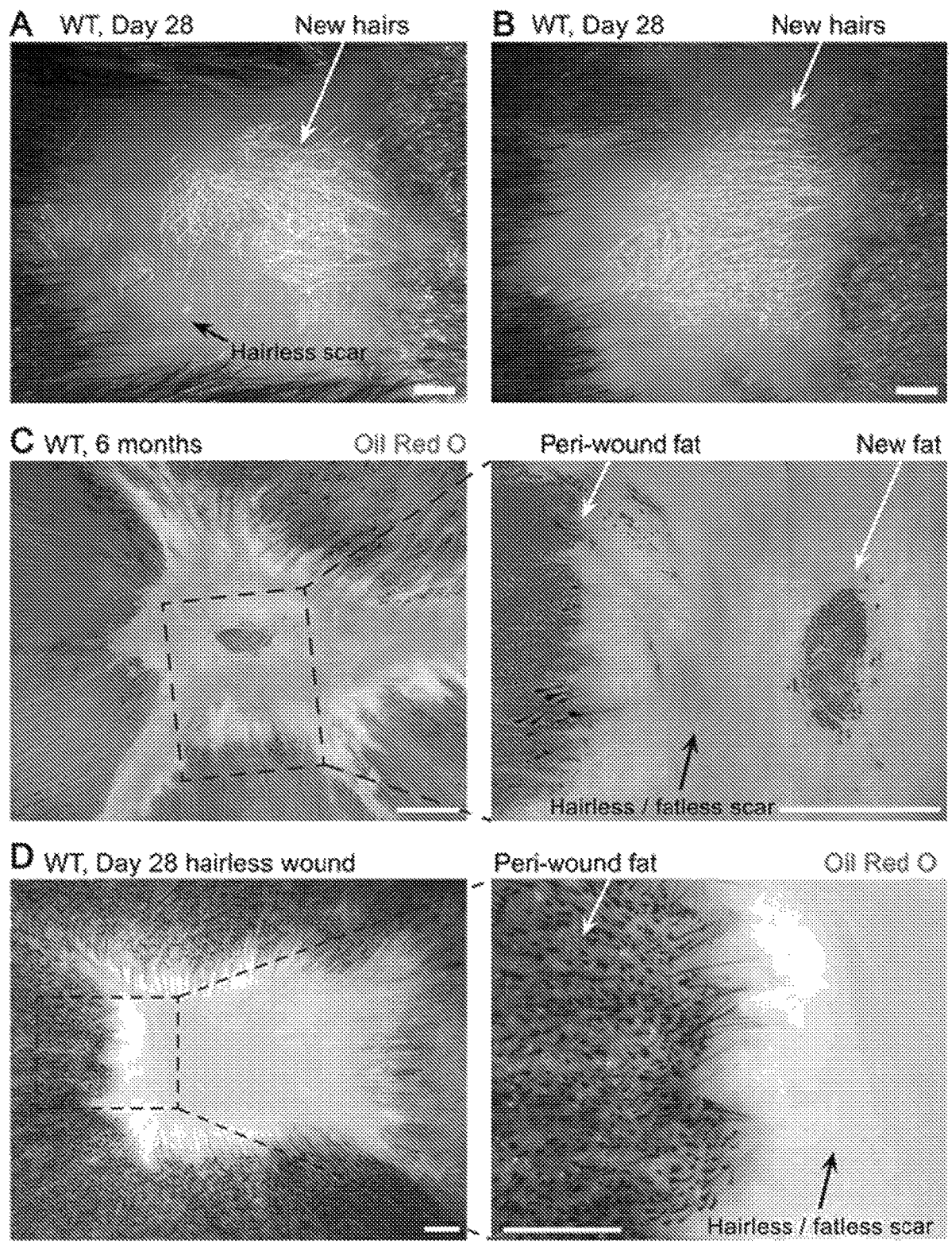
FIG. 5: Wound induced new hair follies and new fat. (A-B) View from skin surface. In large wounds, many new hair follicles regenerate in the center and commonly lack pigmentation. (C) View of underside of skin. New adipocytes are maintained 6 months post-wounding in close physical proximity to new hair follicles and not in the hairless portions of the scar (enlargement is rotated). (D) New adipocytes do not regenerate in hairless wounds. Wound samples were stained for Oil Red O to detect adipocytes. Size bars: A-D—1 mm.
Figure 6:
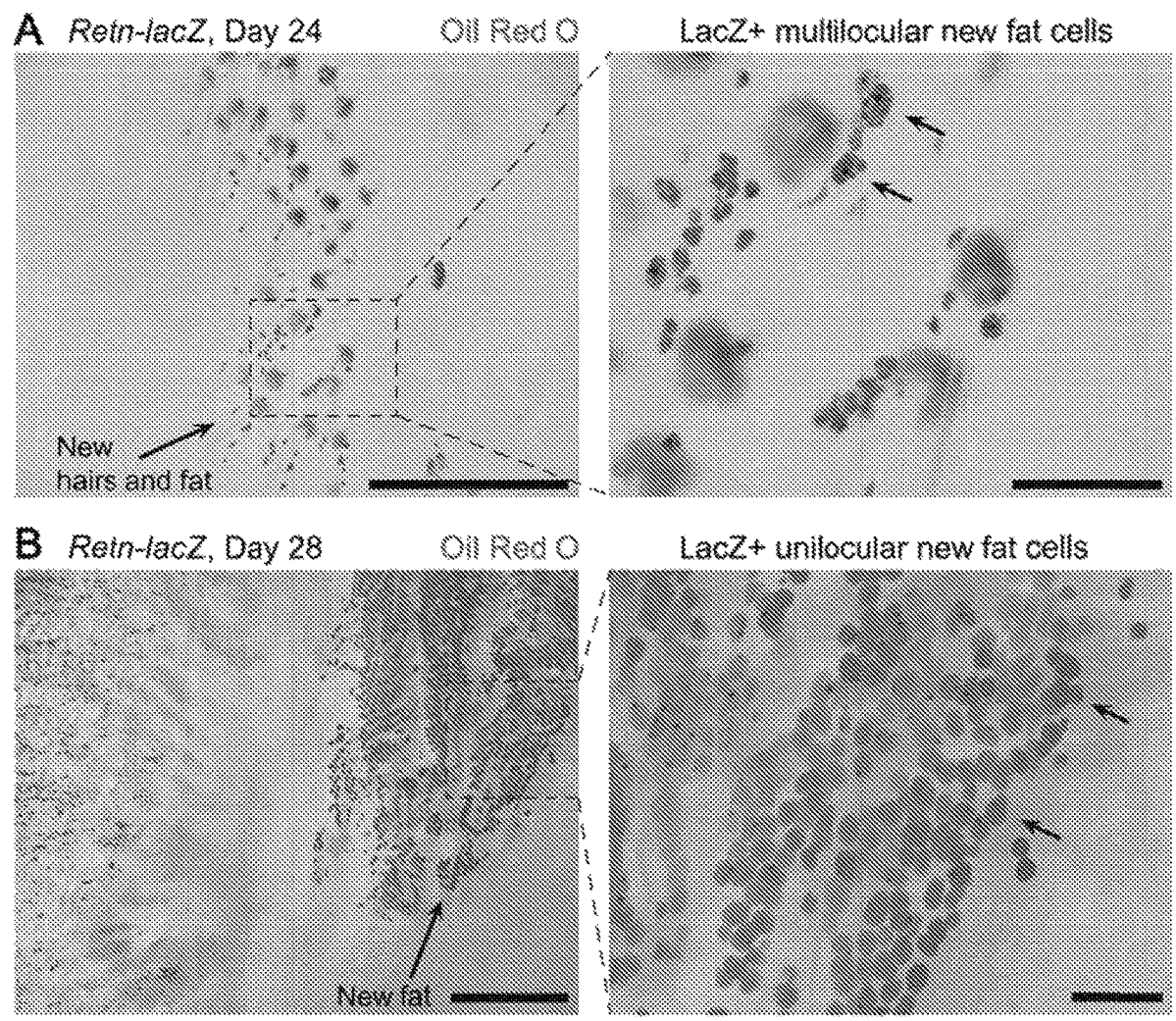
FIG. 6: Maturation of new adipocytes. On day 24 new adipocytes have a multilocular morphology (A), but acquire a unilocular morphology by day 28 (B). Retn-lacZ wound samples were stained for lacZ (nuclear localization, arrows) and counterstained for Oil Red O. Views of underside of skin. Size bars: left panels—1 mm; right panels—200 µm.
Figure 7:
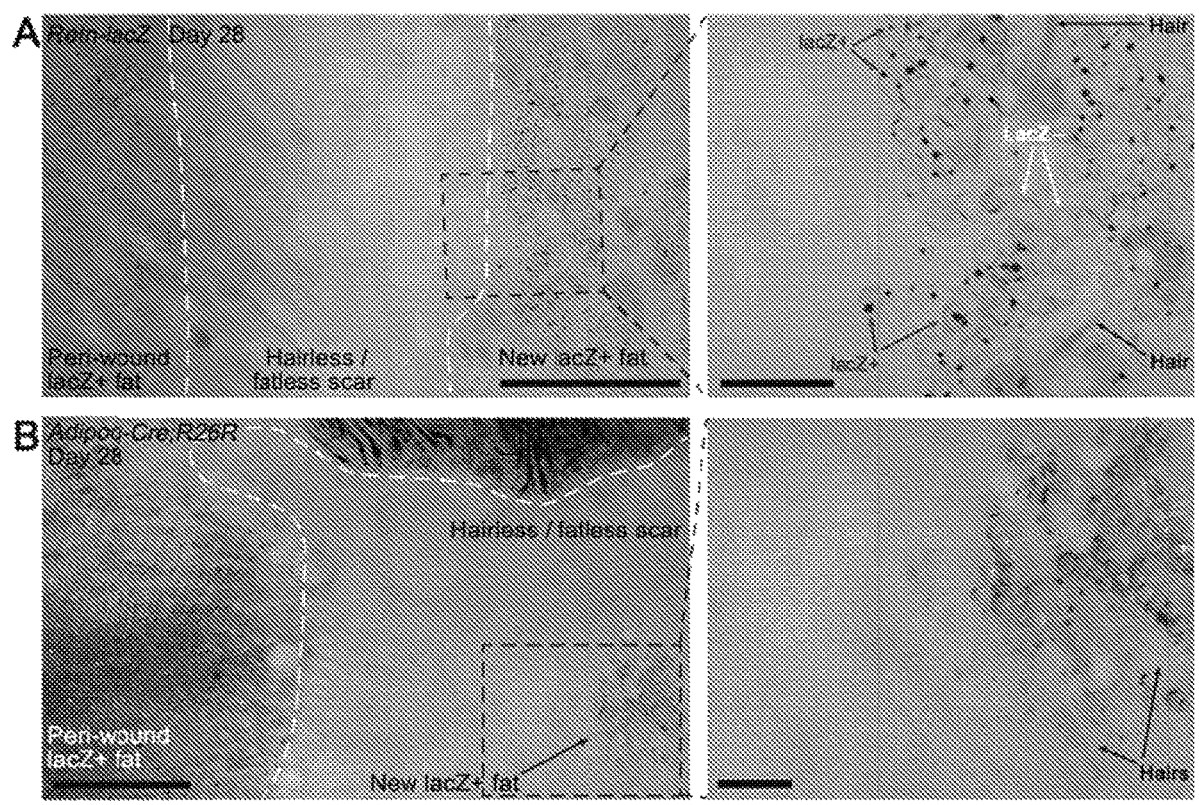
FIG. 7: New adipocytes express the fat-specific hormones resistin and adiponectin. (A) Similar to normal skin adipocytes, new adipocytes in the wound express the fat-specific hormone resistin as seen in Retn-lacZ mice expressing nuclear lacZ. (B) In the skin of Adipoq-Cre;R26R mice, both normal adipocytes at the wound edge and new adipocytes in the wound center express lacZ. Note lack of lacZ positive cells in hairless portion of the scar. Views of underside of skin. Size bars: left panels—1 mm; right panels—200 µm.

Wound healing in adult humans and mice generally results in a scar with excess collagen and absence of hair follicles and cutaneous fat (Example 3 below). Recently, it was discovered that a large skin wound in an adult mouse often regenerates hair follicles under the control of the Wnt and FGF pathways (FIG. 5). It was then noticed new adipocytes within the healed wound indistinguishable from normal cutaneous fat cells in terms of size, density, and depth from the skin surface (FIG. 1A, B; FIG. 5C). The new adipocytes never formed in the hairless part of the wound, but developed exclusively around new hair follicles (FIG. 1B, 5C). Regenerated hair follicles begin to form around 14 days post-wounding, following reepithelialization. The first new adipocytes (orange) appear at 23 days immediately adjacent to the growing hair follicle (blue), and their number and size increase over the next few days (FIG. 1A, FIG. 6). The new adipocytes are physiologically mature and metabolically active white adipose cells because they express fat tissue-specific hormones, resistin and adiponectin, detected as lacZ-positive cells in Retn-lacZ mice (n=9) (FIG. 6, 7A) and in Adipoq-Cre;R26R mice respectively (n=8) (FIG. 7B).

Figure 8:
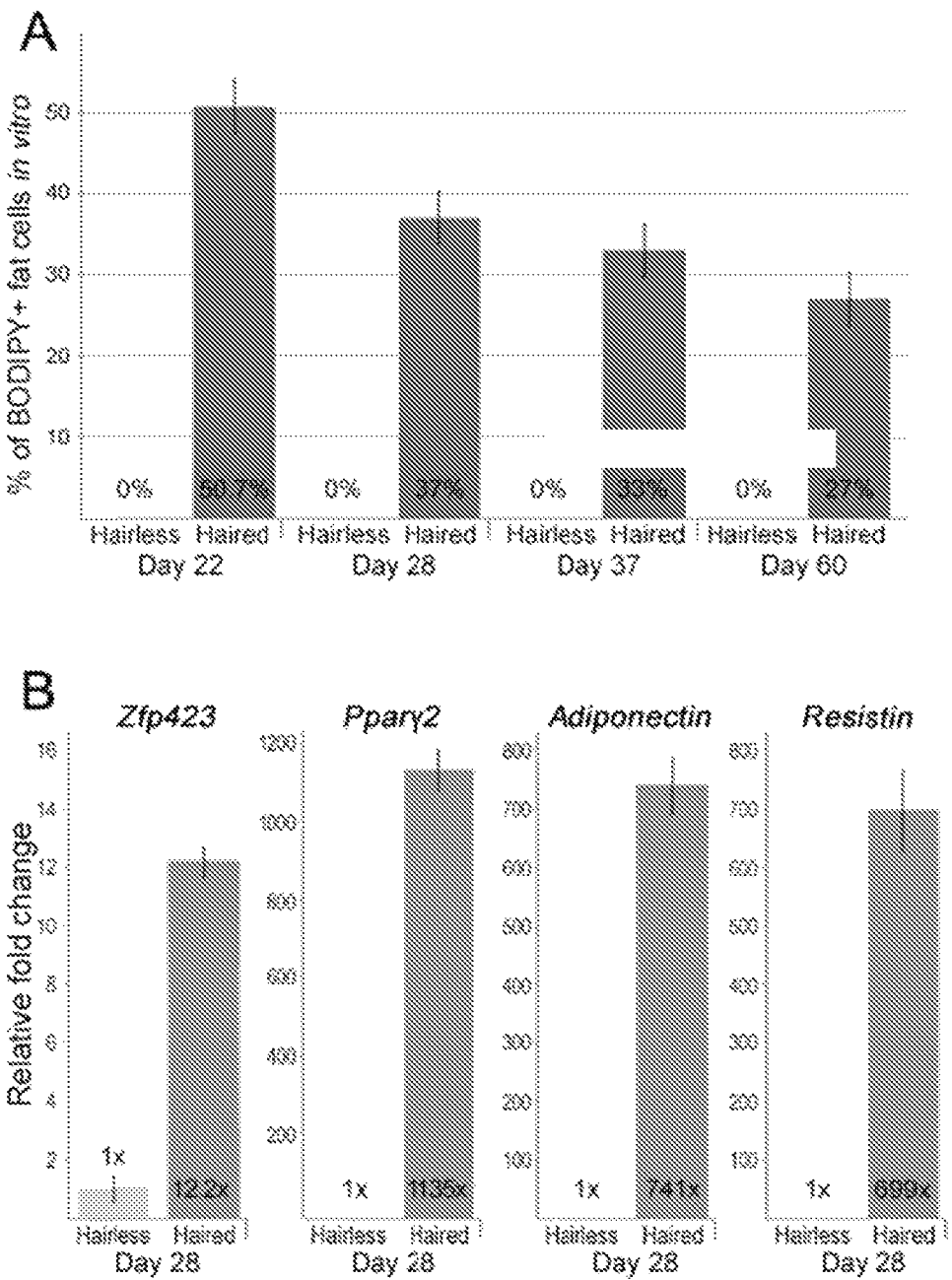
FIG. 8: New adipocytes only regenerate around new hair follicles. (A) Quantitation of adipocytes as percentage of total cultured dermal cells from haired and hairless wounds at different times. (B) In vitro adipogenesis confirmed by differential expression of white adipose-specific genes, Zfp423, Pparg2, Adiponectin, Resistin.

Given the close spatial and temporal association between regenerated hair follicles and regenerated fat, it was asked if hair follicles were necessary to establish adipocyte precursors. To test for such precursors, dermal cells from the wound were placed in a culture that promotes adipocyte differentiation. Dermal cells from wounds with regenerated hair follicles differentiated into lipid-laden adipocytes, but dermal cells from wounds without hair follicles did not (FIG. 1C). Efficient in vitro differentiation and adipose gene upregulation were consistently induced from dermal cells that originated from hair-bearing, but not hairless wounds at different post-wounding time points and as early as 22 days (FIG. 1C, 8).

Figure 2:
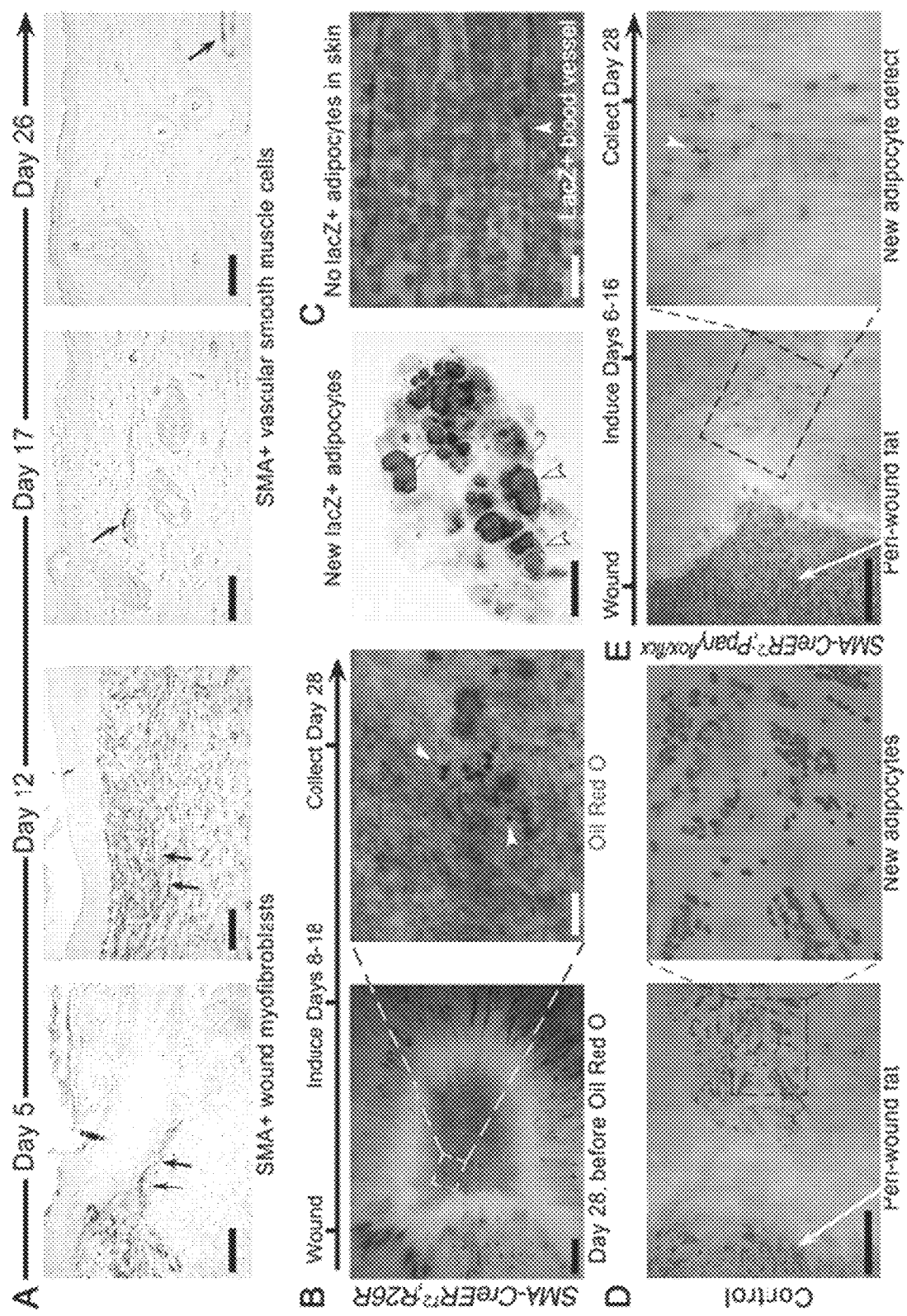
FIG. 2: New adipocytes originate from wound myofibroblasts. (A) Smooth muscle actin (SMA) positive myofibroblasts are present at the wound edge and then in the healing wound (arrows). By day 17, dermal wound cells express very little SMA, but vascular smooth muscle cells remain labeled (arrow). (B) Lineage tracing of myofibroblasts results in lacZ (blue) expressing regenerated adipocytes (orange, white arrowheads). Adipocytes in normal skin are not labeled (C). (D, E) Deletion of Pparγ in myofibroblasts resulted in near complete loss of new adipocytes, whereas normal cutaneous adipocytes at the wound edge remained intact. Size bars: A—100 µm; B (left), D, E—1 mm; B (center)—200 µm; B (right)—50 µm.
Figure 9:
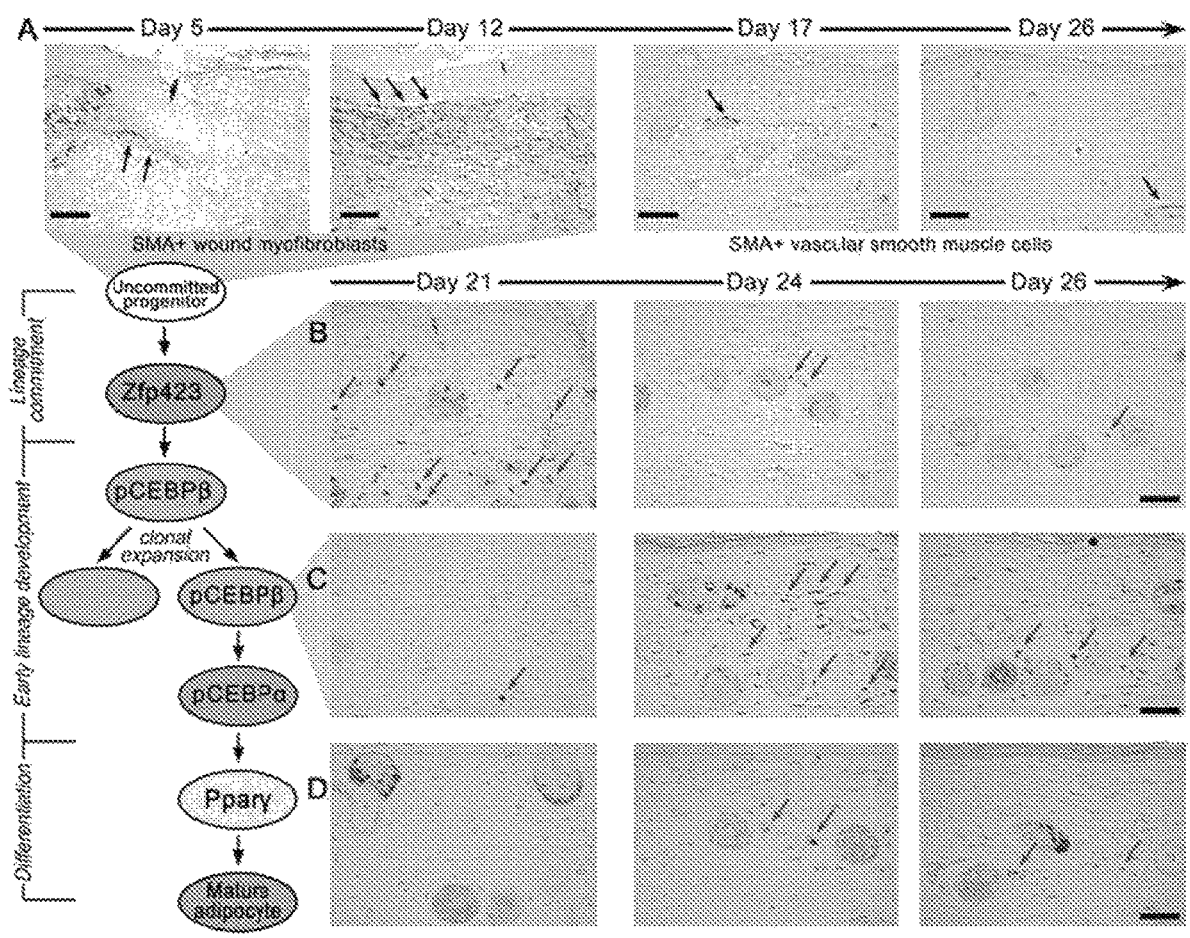
FIG. 9: New adipocytes temporally express characteristic developmental markers for adipocytes. (A) SMA positive myofibroblasts are present at the wound edge at day 5 and then in the wound center at day 12. By day 17, dermal cells express very little SMA. On days 21 and 24, dermal cells expressing adipocyte precursor markers, Zfp423 and pCEBβ, (B, C), and then the adipocyte differentiation marker, Pparγ, appear sequentially (D). Size bars: A-D—100 µm.
Figure 10:
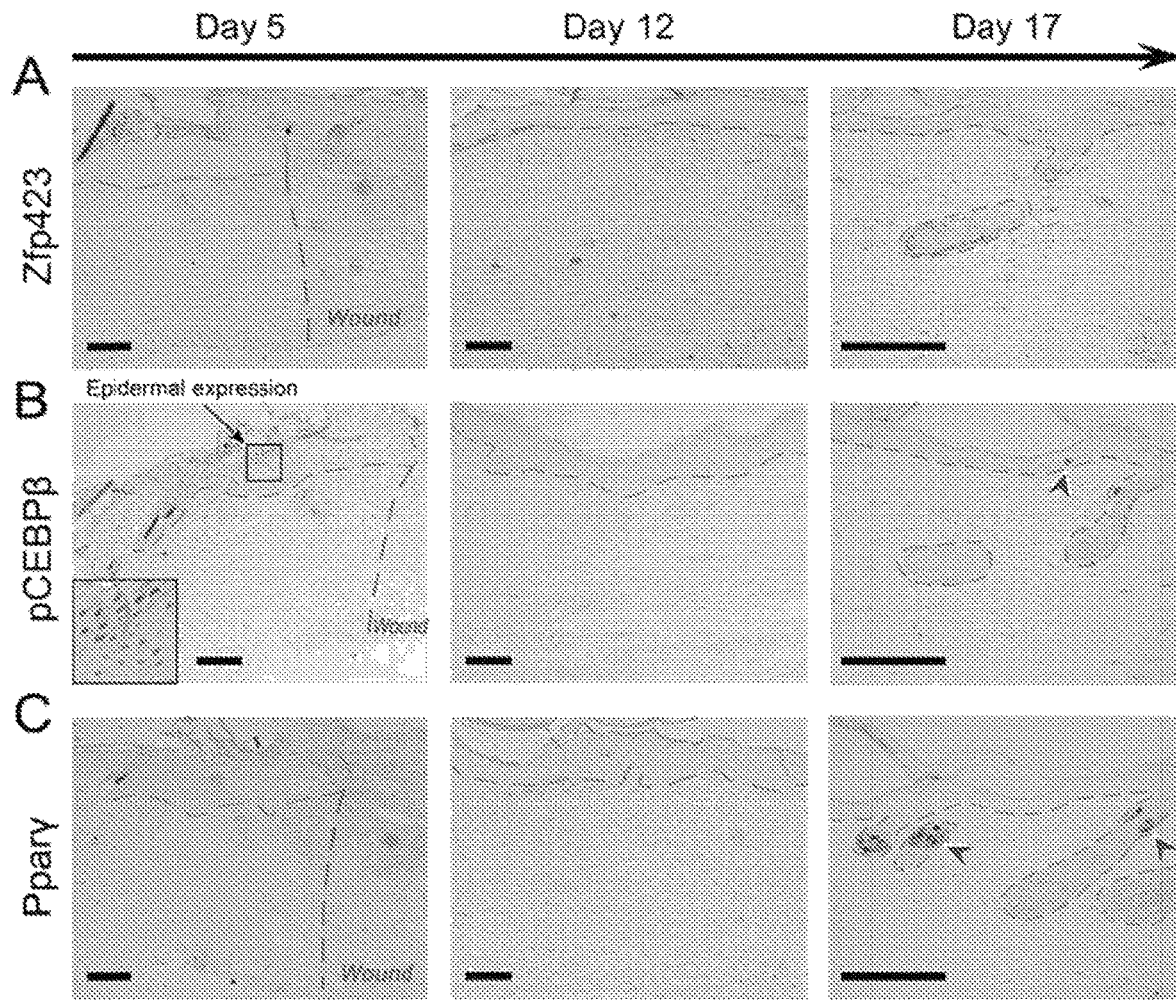
FIG. 10: Expression of adipogenic markers in early stage wounds. Zfp423 (A), pCEBPβ (B) and Pparγ (C) are not expressed in large skin wounds on days 5, 12 and 17. Blue arrowheads mark expression in epithelial compartments, including epidermis and sebaceous glands. Size bars: A-C—100 µm.
Figure 11:
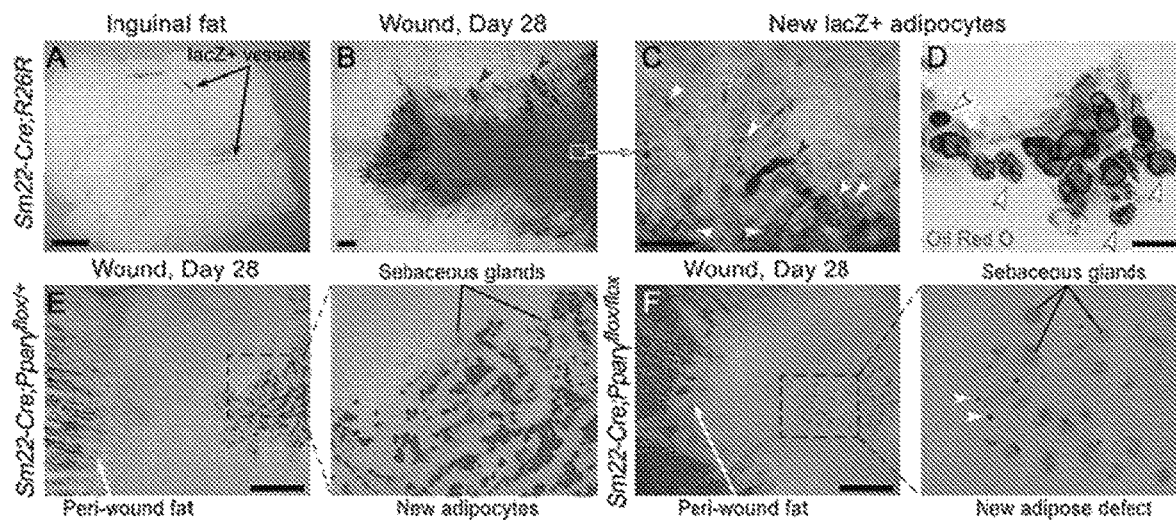
FIG. 11: New adipocytes in the wound arise from Sm22-Cre positive cells. (A-D) New adipocytes (white arrowheads in C and D) express lacZ in Sm22-Cre;R26R mice. This contrasts with the lack of expression in normal cutaneous (B) and visceral fat cells (A). Other expression sites of Sm22-Cre in the wound include blood vessels, dermal papillae (green arrowhead in C) and epithelial outer root sheath of some wound and peri-wound hair follicles (blue arrowheads on B and C). LacZ positive new adipocytes in D were counterstained for Oil Red O. (E, F) Sm22-Cre driven deletion of Pparγ results in the near complete loss of new adipocytes, while normal skin adipocytes at the wound edge develop properly. Formation and growth of new hair follicles in Sm22-Cre;Pparγ$^{flox/flox}$ mice is largely unaffected. Wound samples were stained for Oil Red O. Views of underside of skin. Size bars: A, B, E, F—1 mm; C—200 µm; D—50 µm.
Figure 12:
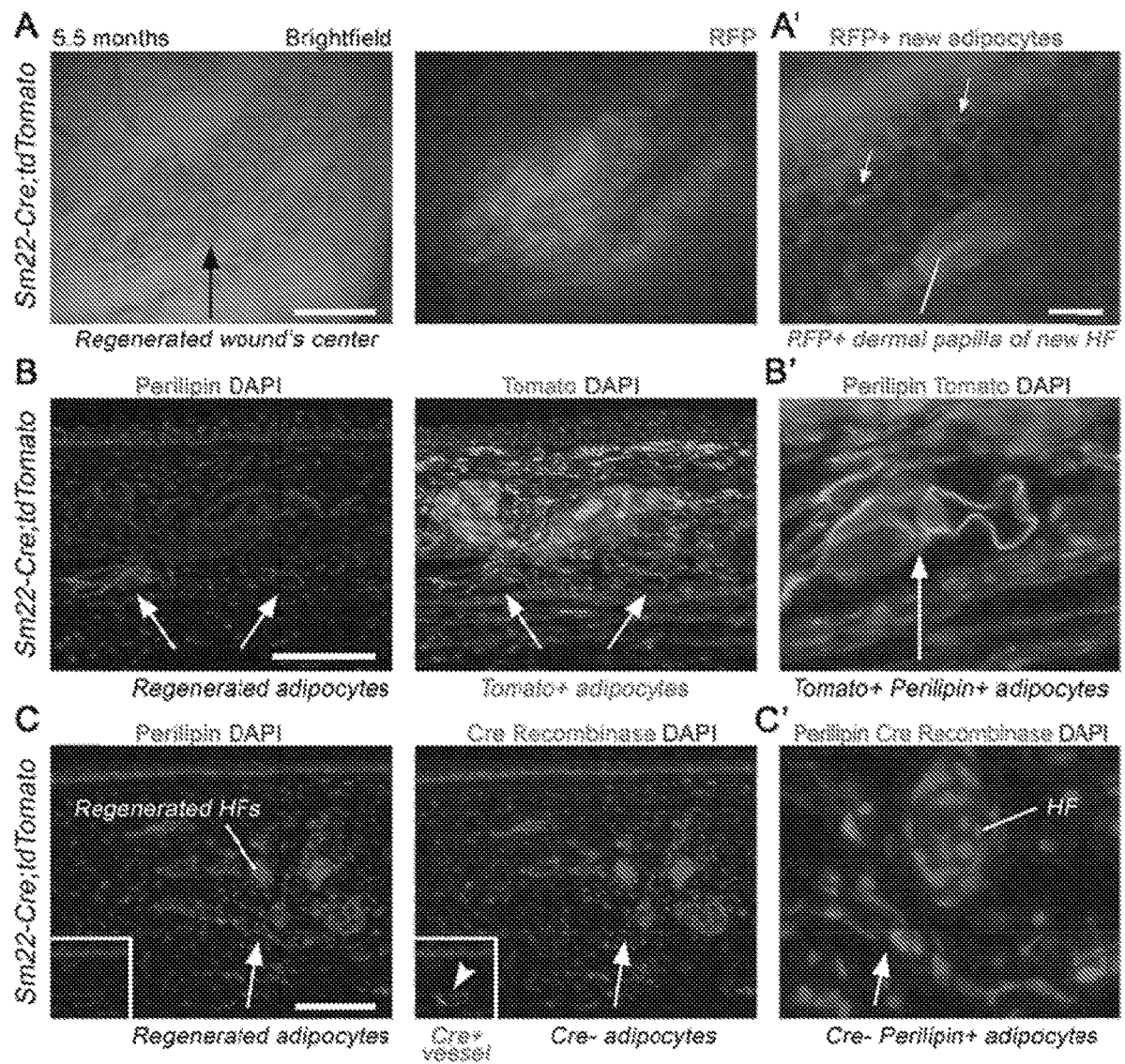
FIG. 12: Sm22-Cre expressing cells give rise to new adipocytes in the wound. (A, A') New adipocytes (white arrows in A') express red-fluorescent reporter in Sm22-Cre;tdTomato mice indicating that they originate from myofibroblasts. Views of underside of skin. (B, B') New adipocytes in Sm22-Cre;tdTomato wounds (white arrows) co-express adipocyte marker Perilipin (red) and tdTomato (green) confirming that they originate from myofibroblasts. (C, C') New Perilipin-positive adipocytes (red) in Sm22-Cre:tdTomato wounds do not co-express Cre Recombinase (green) confirming that they no longer activate Sm22-Cre. Insert shows positive Cre Recombinase expression (green) on the blood vessel in the wound. Size bars: A—1 mm; A'—200 µm; B, C—100 µm.

To determine the cellular origin of the new adipocytes, it was considered that during early wound repair, dermal wound tissue contains many myofibroblasts expressing smooth muscle actin. Myofibroblasts appear in large excisional wounds on day 5 and become abundant in the dermal scar tissue by day 12. These cells largely cease to express smooth muscle to actin by day 17 (FIG. 2A). Cells expressing the adipogenic commitment factors Zfp423 (FIG. 9B, 10A) and pCEBPI (FIG. 9C, O1B) appear adjacent to the new hair follicles at days 21 and 24, respectively. This sequence suggested that myofibroblasts assume an alternative cell fate by converting to adipogenic precursors. To test this, the lineage identity of new adipocytes were examined in SM22-Cre;R26R and inducible SMA-CreER$^{T2}$;R26R mice in which Cre activity turns on in wound myofibroblasts (FIG. 2B, 11B-D). In normal depots of white fat, SM22-Cre and SMA-CreER$^{T2}$ are not activated in adipocytes (FIG. 2C, 11A). However, in wounds of SM22-Cre (n=12) and SMA-CreER$^{T2}$;R26R (n=4) mice induced during wound healing, most new adipocytes expressed LacZ, indicating their origin from myofibroblasts (also see FIG. 12, 15).

Figure 13:
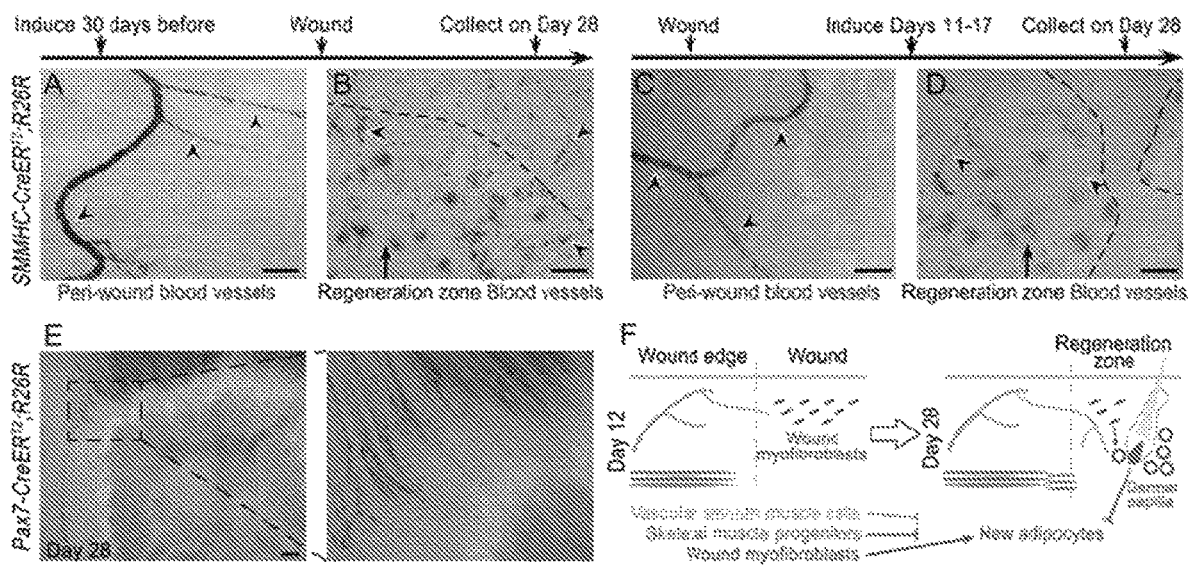
FIG. 13: Among wound myofibroblasts, vascular, and muscle cells adjacent to the wound, only wound myofibroblasts give rise to new adipocytes. (A-D) SMMHC expressing vascular smooth muscle cells do not contribute to new adipocytes as confirmed by lineage tracing in the wounds of SMMHC-CreER$^{T2}$;R26R mice induced either 30 days prior to to wounding (A, B) or between days 11-17 after wounding (C, D). With both induction protocols, lacZ positive cells remain restricted to wound and peri-wound blood vessels (arrowheads). (E) Pax7 expressing satellite stem cells of the panniculus *carnosus* muscle do not contribute to new adipocytes as confirmed by lineage tracing in the wounds of Pax7-CreER$^{T2}$;R26R mice induced one week prior to wounding. LacZ labeled cells remain restricted to regenerating skeletal muscle fibers. (F) Schematic representation of contractile cell types in and around regenerating wounds. Among heterogeneous contractile cell types, only wound myofibroblasts contribute progenitors toward new fat tissue. Views of underside of skin. Size bars: A-D—200 µm; E—1 mm.

To functionally validate a myofibroblast-to-adipocyte transformation, the loss-of-function SM22-Cre;Pparγ$^{flox/flox}$ and inducible SMA-CreER$^{T2}$;Pparγ$^{flox/flox}$ mice were generated. Wounds of SM22-Cre;Pparγ$^{flox/flox}$ mice formed many new hair follicles but were nearly devoid of new adipocytes (n=7, new adipocyte/follicle ratio: 0.62+/−0.2 vs. 24.1+/− 6.8 in control [n=7], FIG. 11F; see Materials and methods). The difference between experimental and control groups was nearly 40-fold (FIG. 11E; Table 1). Importantly, in SM22-Cre;Pparγ$^{flox/flox}$ mice depots of white fat outside the wound, both subcutaneous and elsewhere, were unaffected. Similarly, Tamoxifen induction of SMA-CreER$^{T2}$;Pparγ$^{flox/flox}$ mice during early time points after wounding largely prevented regeneration of adipocytes (n=6, new adipocyte/ follicle ratio: 0.5+/−0.07 vs. 22.7+/−5.1 in control [n=6], FIG. 2D, 2E). Taken together, the lineage tracing studies establish myofibroblasts as the source for new regenerating adipocytes (FIG. 13F).

Figure 14:
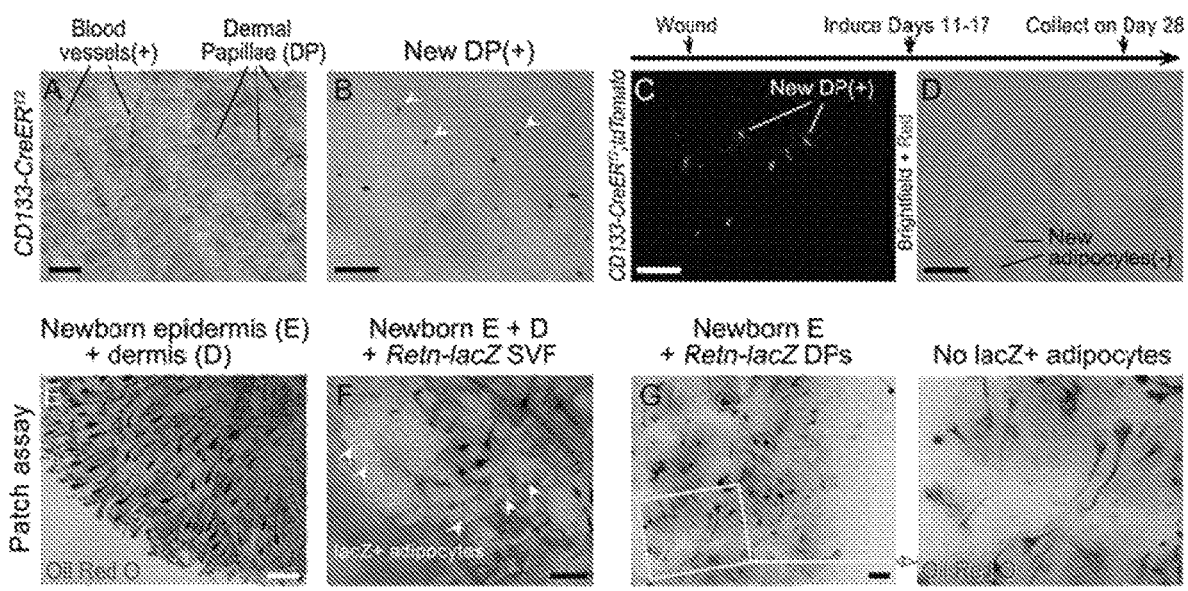
FIG. 14: Dermal papillae of new hair follicles do not possess adipogenic progenitor potential (A, B) Activity of endogenous lacZ reporter in adult CD133-CreER$^{T2}$ mice is restricted to isolated cutaneous blood vessels and to dermal papillae of new (white arrowheads), but not normal peri-wound hair follicles. (C, D) CD133 expressing new dermal papilla cells do not contribute to new adipocytes as confirmed by lineage tracing in the wounds of CD133-CreER$^{T2}$; tdTomato mice induced between days 11-17 after wounding. On day 28, tdTomato labeled cells remain restricted to dermal papillae of new follicles and do not convert into new adipocytes. (E-G) In a hair follicle reconstitution assay, Retn-lacZ vibrissa-derived dermal papilla cells induce formation of new follicles, but do not give rise to lacZ positive adipocytes (G). In contrast, Retn-lacZ WAT stromo-vascular fraction cells contribute lacZ positive adipocytes into reconstituted skin generated with newborn dermis and epidermis (F, arrowheads). Samples on E and G (right panel only) were counterstained for Oil Red O. Views of underside of skin. Size bars: A-G—200 µm.
Figure 15:
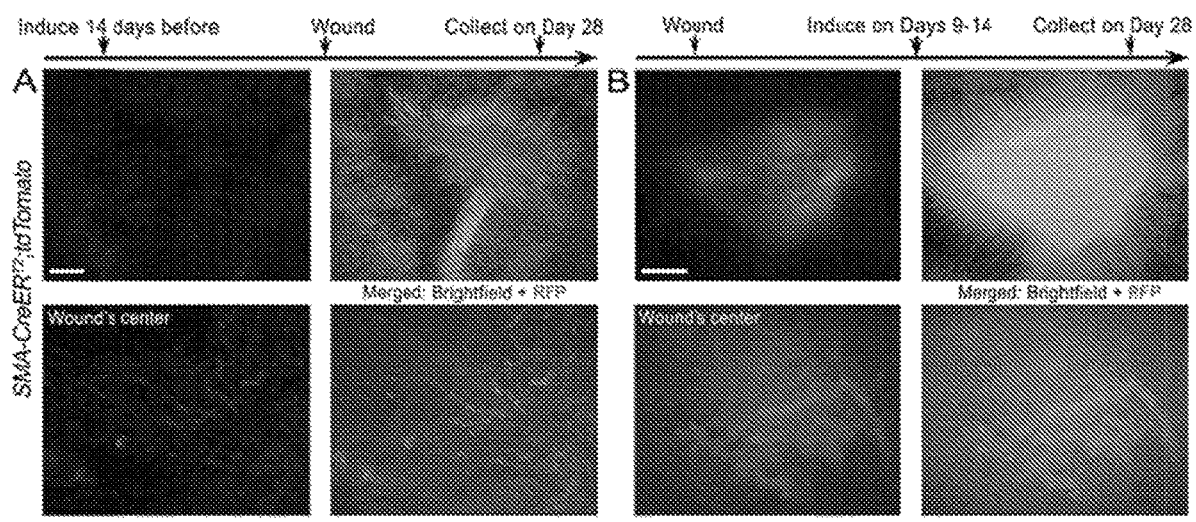
FIG. 15: SMA-CreERn can be used to lineage trace wound myofibroblasts. (A) Cre induction in SMA-CreER$^{T2}$; tdTomato mice 14 days before wounding results in preferential labeling of vascular smooth muscle cells. (B) Induction during days 9-14 after wounding results in labeling of myofibroblasts in the wound center. Views of underside of skin. Size bars: A, B—2 mm.

To evaluate the possible contribution of other SM22/SMA positive cell populations, including vascular smooth muscle cells, panniculus *carnosus* muscle, and dermal papillae of new hair follicles, to fat regeneration, the progeny of these cell populations were traced using relevant promoter systems. No contribution of these cell types to new adipocytes was found (FIGS. 13, 14; Example 5 below).

Figure 21:
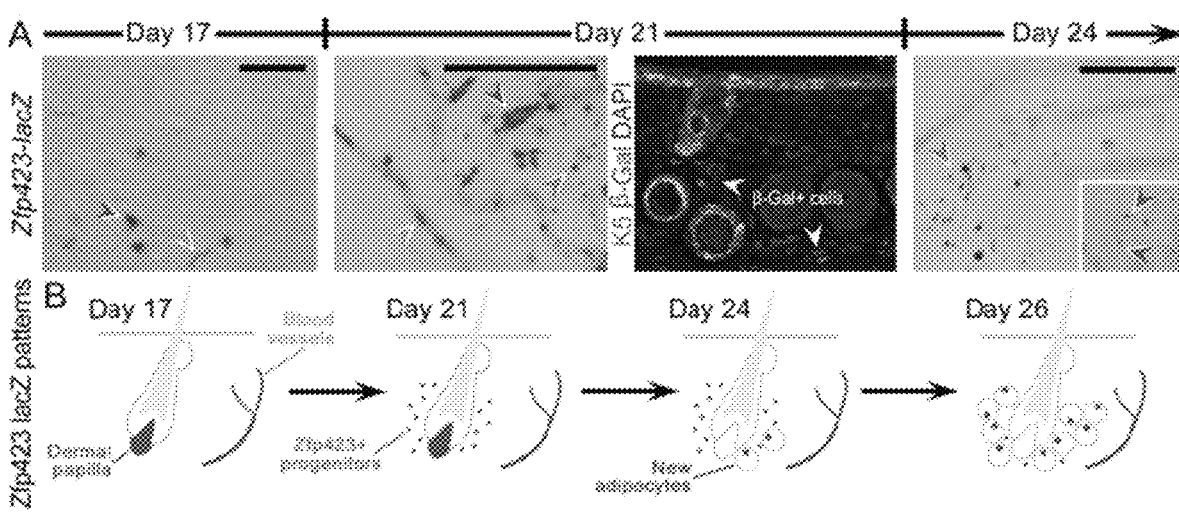
FIG. 21: Spatio-temporal patterns of Zfp423 activity (lacZ expression) in the wounds of Zfp423-lacZ mice. (A) Zfp423 activity (blue) was detected in dermal papilla of new hair follicles (green arrowheads), in blood vessels (orange arrowheads) and in dermal cells (purple arrowheads) surrounding new hair follicles starting at wound day 21. On wound day 24, new adipocytes (red arrowheads) also express Zfp423 activity. Note that wound day 24 panel is an enlargement of FIG. 22B (same sample). (B) Schematic depiction of Zfp423 reporter patterns seen in regenerating wounds. Size bars: A—200 µm.

To comprehensively study the molecular nature of lineage reprogramming of myofibroblasts to adipocytes in adult wounds, the transcriptomes of wound myofibroblasts were profiled by RNA-sequencing (FIGS. 3A-3C, 16-19; Examples 6-9 below). Among 4,120 differentially expressed genes (FIG. 3B), at the onset of adipocyte regeneration several transcriptional regulators of the adipocyte lineage, including Zfp423, Crebl2, Stat5b and Klf15, were upregulated, whereas transcriptional regulators of chondrogenic and osteogenic lineages, including Sox9/11, Runx1/2, Fhl2 and Pitx1, were downregulated (FIG. 18; Example 7 below). The Zfp423 transcription factor, which drives commitment of mesenchymal progenitors toward the adipocyte lineage during embryogenesis was expressed by dermal cells juxtaposed to regenerated hair follicles starting on day 21 after wounding (FIG. 21, 22A). Then, the number of Zfp423$^+$ dermal cells increased, before diminishing by 28 days coincident with the increase in mature adipocytes (FIG. 21, 22B, 22C).

Figure 20:
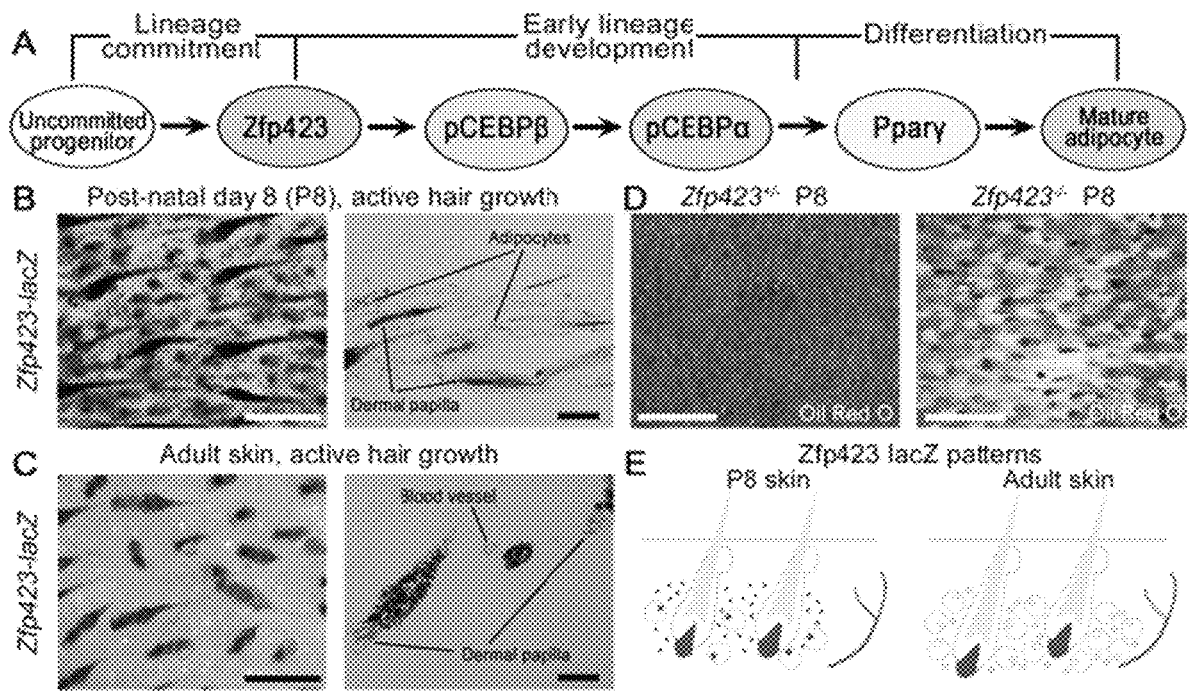
FIG. 20: Normal adipogenesis during skin development depends on Zfp423. (A) Schematic representation of the key signaling events in white adipose lineage development. (B, C) LacZ expression in Zfp423-lacZ reporter mice reveals transcriptional activation of Zfp423 in dermal cells around hair follicles at post-natal day 8 (B), but not in adult skin during active hair growth (C). Note that the Zfp423 reporter is also active in dermal papillae and blood vessels. (D) At post-natal day 8, the cutaneous fat layer in dorsal skin of Zfp423 null mice appears thinner than in control, but hair follicles develop normally. (E) Schematic representations depicting differences in Zfp423 reporter activity between developing and mature skin. Views of underside of skin. Size bars: B, C, D—200 µm.

The temporal changes in Zfp423 expression suggested that wounding activated this embryonic pathway to facilitate adipocyte regeneration. Supporting this hypothesis, adult Zfp423 mutant mice failed to regenerate fat completely despite forming many new hair follicles after wounding (n=9, new adipocyte/follicle ratio: 0.07+/−0.06 vs. 29.6+/− 5.4 in control [n=9], FIG. 3D). The critical role of Zfp423 for reprogramming myofibroblasts during wounding in the adult was in contrast to its non-essential role for adipocyte development in the embryo since Zfp423 mutant mice possess skin adipocytes (FIG. 20), likely due to compensation by redundant pathways apparently available during development but not regeneration.

Figure 23:
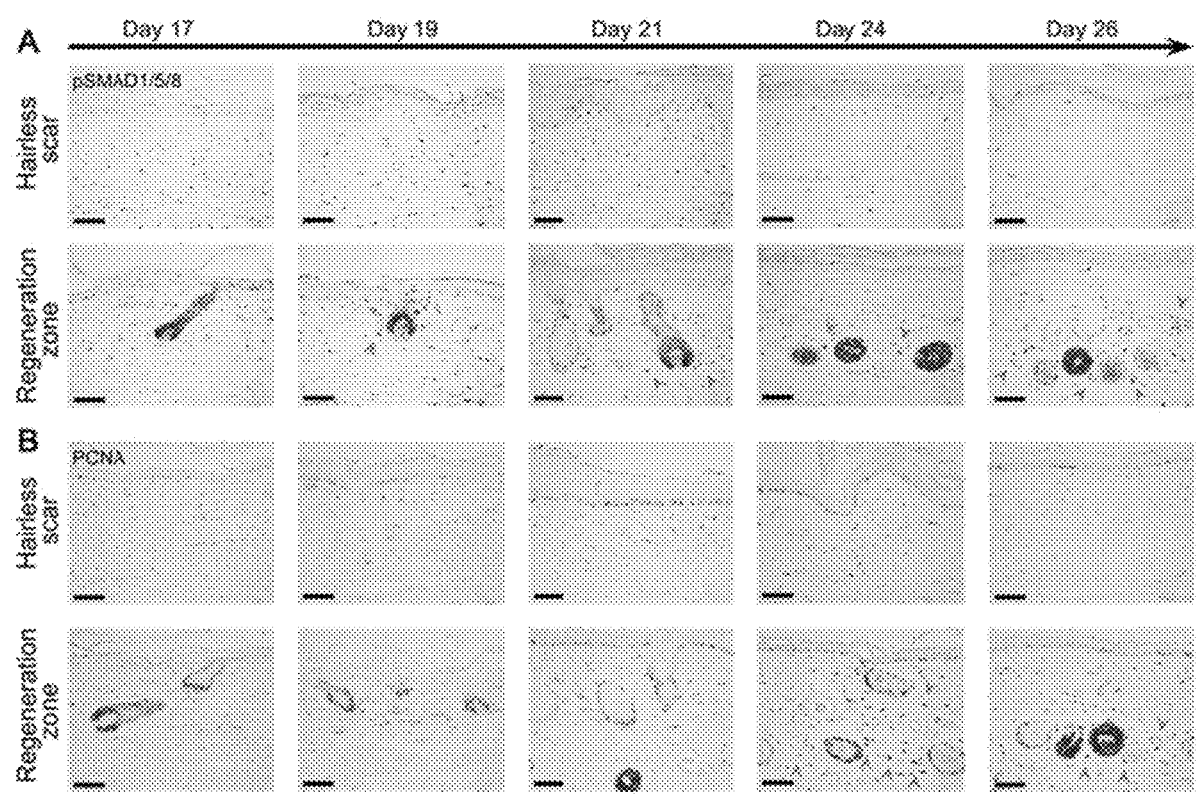
FIG. 23: Patterns of proliferation and BMP signaling during new fat regeneration. Large numbers of both pSMAD1/5/8 positive (A) and PCNA positive cells (B) appear in hair-bearing, but not hairless portions of the wound scar tissue on days 24 and 26 (purple arrowheads). Size bars: A-B—50 µm.

To determine the molecular regulation of reprogramming, it was considered that bone morphogenetic protein (BMP) signaling induces adipogenic commitment of cells in vitro, and that actively growing hair follicles, which are critical for myofibroblast-to-adipocyte reprogramming, strongly express Bmp2 and Bmp4. The transcriptomic data also shows that endogenous BMP ligands, Bmp2 and Bmp7, are upregulated, whereas the soluble BMP antagonists, Bambi and Grem1, are downregulated in myofibroblasts by day 21 (FIG. 18; Example 8 below). Marked upregulation of pSMAD1/5/8 expression, indicators of active BMP signaling, was also noted in dermal cells next to regenerated hair follicles at day 21 (FIG. 23A), at the time of Zfp423 activation.

Figure 24:
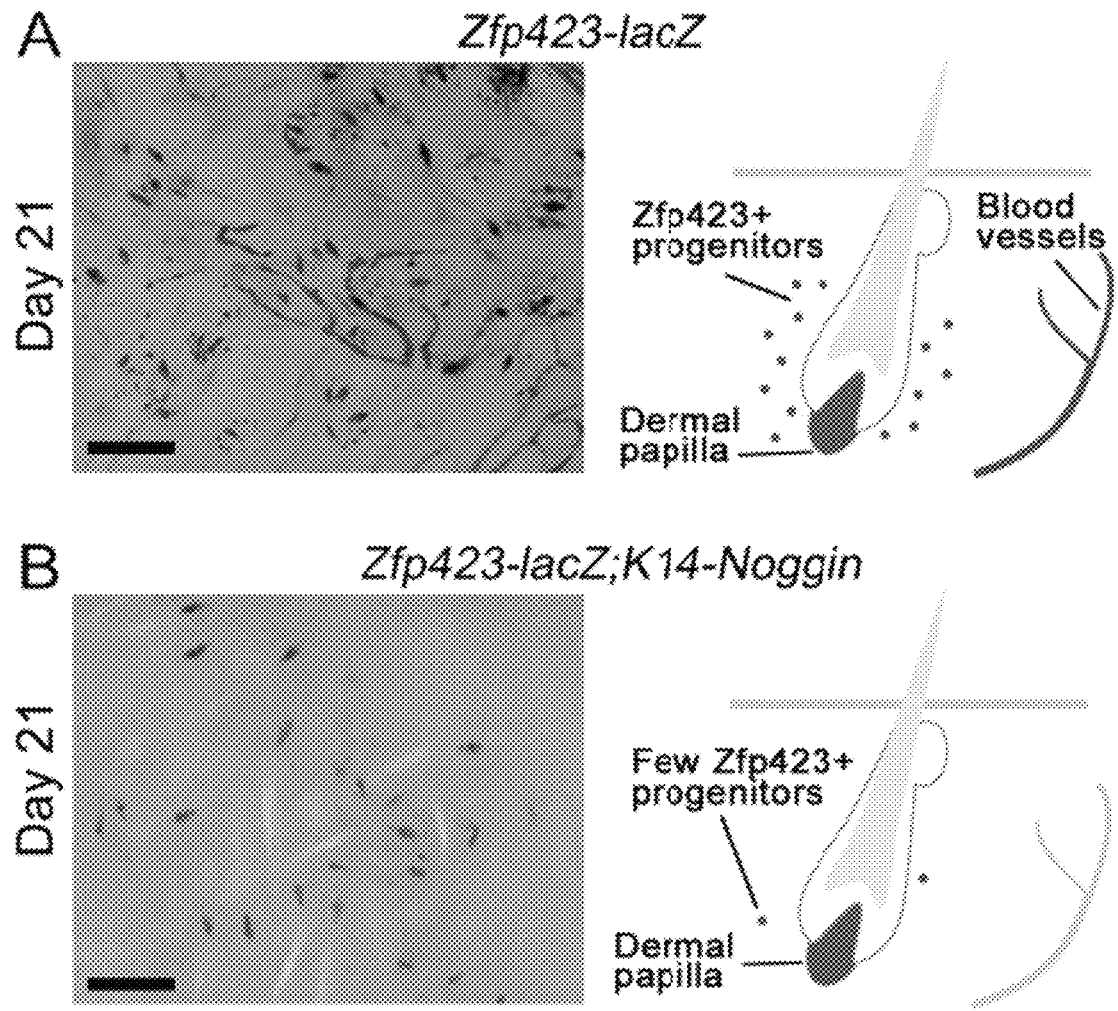
FIG. 24: BMP signaling Is necessary for Zfp423 reporter activation in regenerating wounds. (A, B) In K14-Noggin mice, which overexpress the soluble BMP antagonist noggin, Zfp423 activity becomes significantly downregulated on day 21 in dermal wound cells surrounding new hair follicles, as well as in blood vessels. Size bars: A, B—200 µm.
Figure 25:
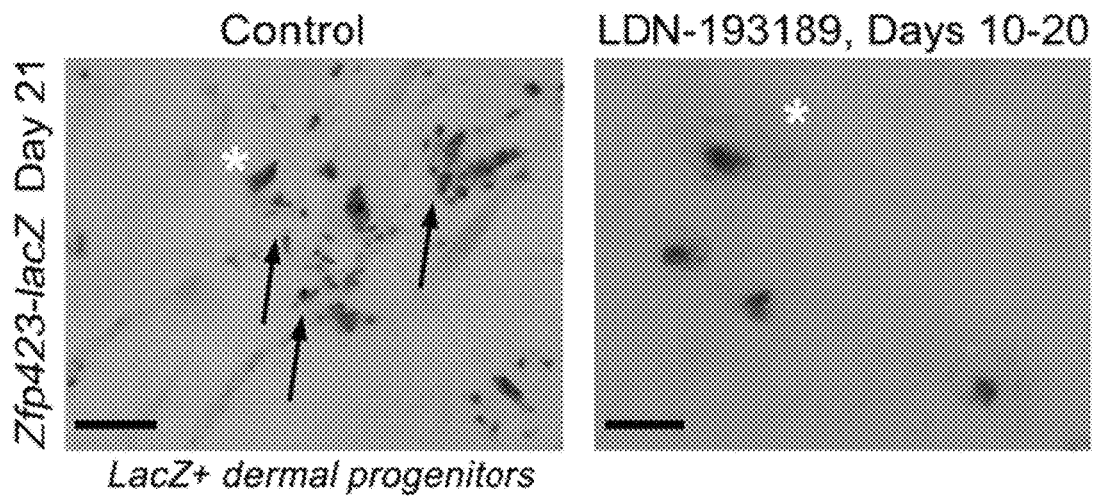
FIG. 25: BMP signaling is necessary for Zfp423 reporter activation in wounds. Treatment with the BMP antagonist, LDN-193189 (2 mg/kg), during wound healing significantly downregulated Zfp423 activity on day 21 in dermal cells surrounding new hair follicles, and in blood vessels. Asterisk marks lacZ-positive dermal papillae of new hair follicles. Size bars: 100 µm.

To test whether BMP signaling is modulating adipocyte regeneration, K14-Noggin mice, which overexpress noggin, a soluble BMP antagonist, in the epithelial cells of the hair follicle were studied. After wounding, these mice failed to regenerate fat despite forming normal appearing hair follicles (n=10, new adipocyte/follicle ratio: 0.2+/−0.1 vs. 30.6+/−6.3 in control [n=10], FIG. 3E). Similarly, treatment of mice during wound healing with a small-molecule inhibitor of SMAD1/5/8 phosphorylation largely prevented new adipocyte regeneration in hair-bearing wounds (n=7, new adipocyte/follicle ratio: 0.58+/−0.35, FIG. 3G). Zfp423 reporter activity was downregulated in the K14-Noggin (FIG. 24) and inhibitor treated mice (FIG. 25), indicating that BMP was activating Zfp423 in myofibroblasts.

Figure 3:
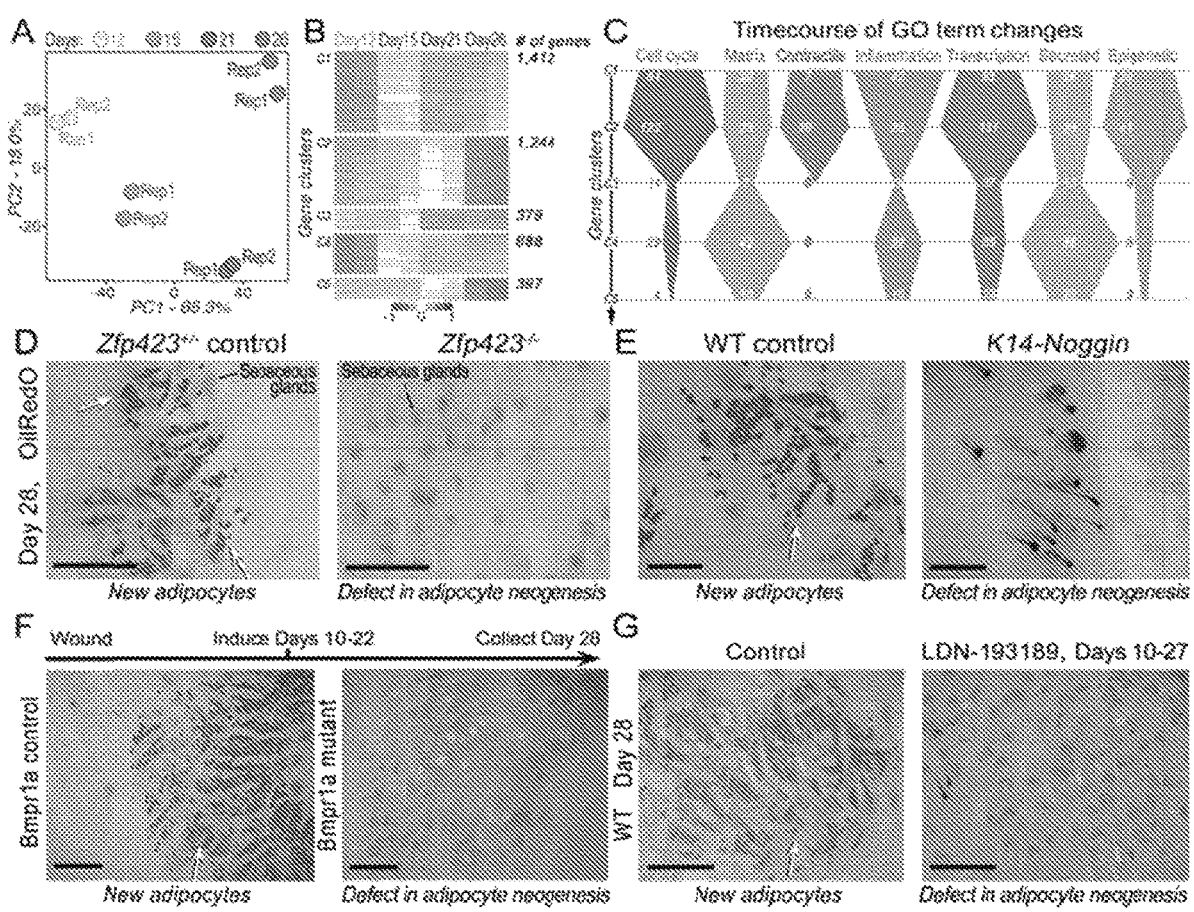
FIG. 3: Molecular profiling and functional studies of adipocyte regeneration reveal Zfp423 and BMP signaling necessary for adipocyte regeneration. (A) Principal component analysis of myofibroblast transcriptome reveals distinct changes across four post-wounding time points. (B) 4,120 differentially expressed genes from day 12-26 myofibroblasts group into five distinct clusters. (C) Differentially expressed genes in several gene ontologies undergo to distinct temporal changes in myofibroblasts. Deletion of Zfp423 (D), overexpression of the soluble BMP antagonist noggin in K14-Noggin mice (E), SMA-CreER$^{T2}$ driven deletion of Bmpr1a (F), treatment with the BMP antagonist, LDN-193189 (2 mg/kg) during wound healing (G) all resulted in near complete loss of regenerated adipocytes in wounds despite normal regeneration of hair follicles. Size bars: D-G—100 µm.
Figure 4:
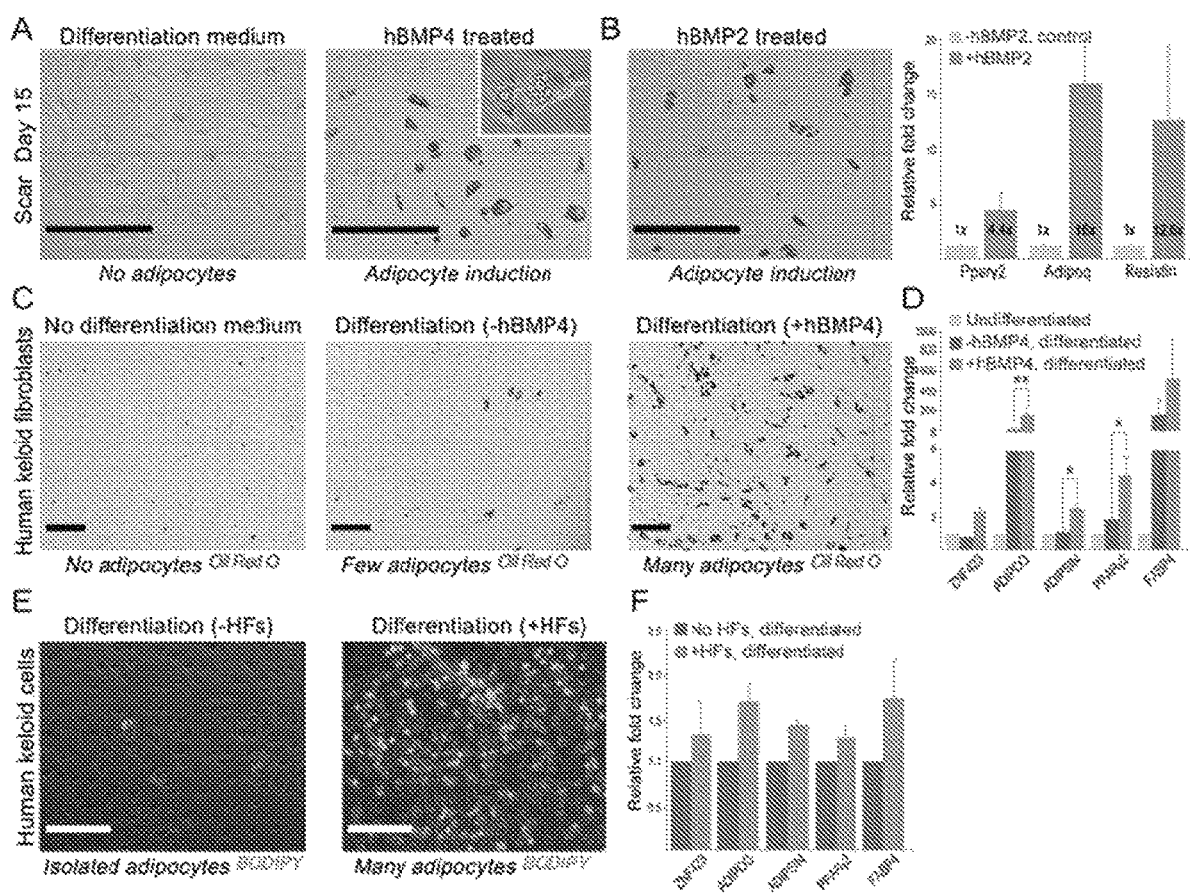
FIG. 4: BMP drives reprogramming of mouse and human myofibroblasts into adipocytes. (A, B) Treatment of cultured mouse dermal cells isolated from day 15 wounds either with human recombinant BMP4 or BMP2 induced their reprogramming into adipocytes and activation of adipocyte-specific genes. Day 15 dermal cells cultured in pro-adipogenic differentiation media without BMP remained non-adipogenic. (C, D) Treatment of cultured human keloid scar cells with human recombinant BMP4 and adipocyte differentiation media induced their reprogramming into adipocytes with activation of adipocyte-specific genes. In a co-culture system, human scalp hair follicles induced adipogenic conversion of human keloid scar cells (E) with a concomitant increase in adipocyte genes (F). Size bars: A, B—400 µm; C, E—200 µm.
Figure 27:
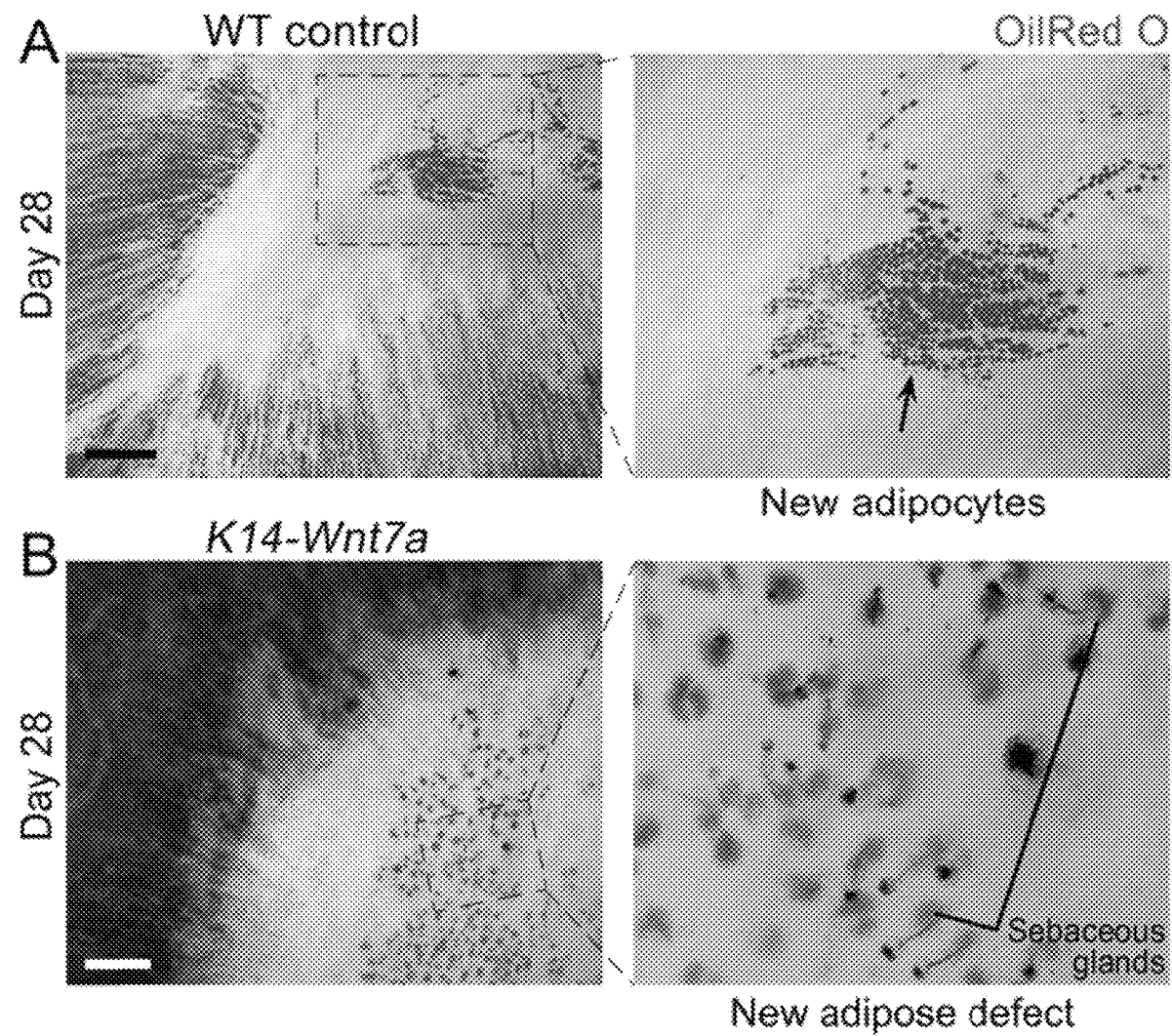
FIG. 27: Overexpression of WNT blocks adipocyte neogenesis in wounds. In contrast to WT control mice (A), in K14-Wnt7a mice overexpressing Wnt7a (B), new adipocytes do not form after wounding despite formation of increased numbers of new hair follicles. Size bars: A, B—1 mm.

To specifically test whether BMP signaling in myofibroblasts was necessary for adipocyte regeneration, the BMP receptor, Bmpr1a, was deleted in SMA-CreERn;Bmpr1a$^{flox/flox}$ mice. This led to a lack of new adipocytes despite the formation of many new hair follicles (n=6, new adipocyte/ new follicle ratio: 0.38+/−0.36 vs. 23.9+/−1.5 in control [n=3], FIG. 3F). In addition, exposing myofibroblasts from early wounds to BMP in vitro reprogrammed them toward an adipocyte fate (FIG. 4A, 4B). Since WNTs are known inhibitors of adipocyte differentiation, K14-Wnt7a mice were also examined and lack of fat regeneration despite an increased number of new hair follicles following wounding was discovered (n=6, new adipocyte/new follicle ratio: 0.6+/−0.3 vs. 28+/−4.2 in control [n=6], FIG. 27).

Figure 28:
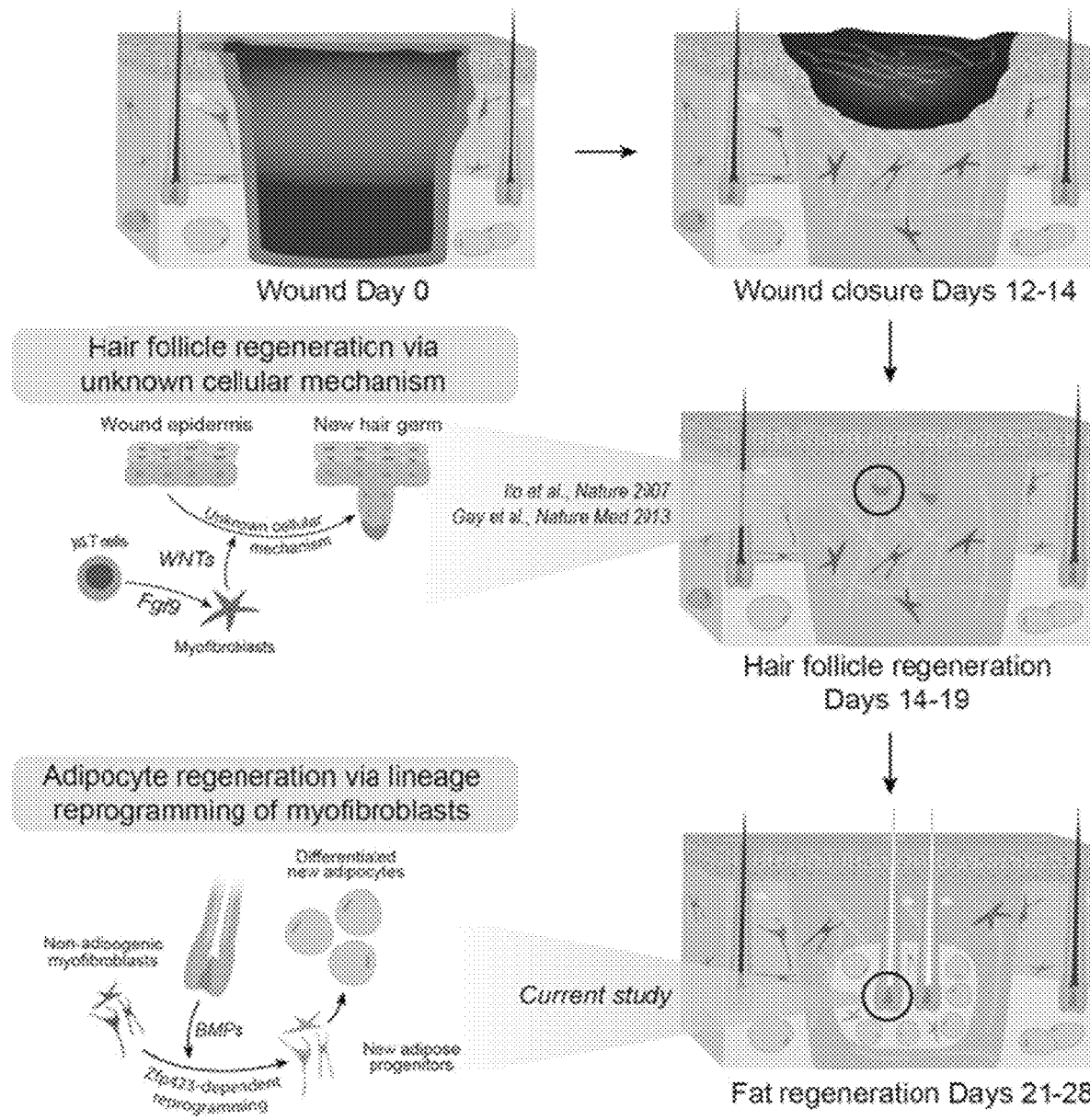
FIG. 28: Proposed model for wound induced hair follicle and fat regeneration in adult skin wounds. New hair follicles regenerate on days 14-19 via an Fgf9/WNT feedback loop-dependent signaling mechanisms. The cellular basis for hair regeneration (i.e. changes in cell lineage identity) remains to be established. The studies here reveal that new adipocytes regenerate on days 21-28 via BMP/Zfp423 driven lineage reprogramming of non-adipogenic to wound myofibroblasts.

To determine relevance of these findings to humans, keloid scar cells in culture were treated with BMP4 and induced their conversion to lipid-laden adipocytes as indicated by expression of adipocyte markers (n=3; FIG. 4C, 4D). Co-culture of human keloid myofibroblasts with human scalp hair follicles also induced their adipogenic conversion (FIG. 4E, 4F; Example 11 below). Taken together, the data suggest that new hair follicles in the wound reprogram myofibroblasts to an adipocyte fate by activation of the BMP-Zfp423 pathway (FIG. 28).

Myofibroblasts, characterized by contractile behavior, excessive collagen deposition, and secretion of profibrotic cytokines are found in many tissues in response to injury and inflammation. Though the developmental origin of cutaneous myofibroblasts continues to be elucidated, at the transcriptome level they are largely distinct from any well-characterized fibroblast populations in unwounded skin, including multipotent skin derived precursors (FIG. 19; Example 10 below), and their scar-promoting properties are thought to be maintained by epigenetic changes, including DNA hypermethylation. Therefore, myofibroblasts were not considered capable of converting to another cell type and their depletion was viewed as a main anti-scarring strategy.

The myofibroblast conversion to adipocytes demonstrates lineage reprogramming in vivo in an adult mammal. Several recent studies have shown that tissue regeneration respects tissue boundaries: epithelium regenerates from epithelium, dermis from dermis and cartilage from cartilage. The findings here reveal the ability of wound myofibroblasts to convert to a completely different adipocyte lineage. The findings support a window of opportunity after wounding to influence the regeneration rather than scarring of tissue by activating embryonic pathways and converting myofibroblasts to adipocytes. This Example shows that hair follicles grow independently of fat and that hair follicle regeneration is necessary and proximal to cutaneous fat regeneration. The transcriptomic and functional data support a key role for BMP, and indicate that strategies for regenerating hair follicles could ultimately benefit patients with disorders lacking fat, such as acute scars, keloids, lipodystrophies, and aging.

Example 3: Additional Lineage Tracing Results

Several non-myofibroblast mesenchymal cell types display SM22/SMA activity in and around the wound bed. These include vascular smooth muscle cells (VSMCs) of the wound and peri-wound blood vessels, subcutaneous skeletal muscle panniculus carnosus and dermal papilla cells of new hair follicles. To definitively establish that myofibroblasts are the key mesenchymal adipogenic progenitors in the wound, a series of additional lineage tracing experiments were performed. First, we took advantage of the fact that not all smooth muscle contractile proteins are expressed in myofibroblasts. Smooth muscle myosin heavy chain (SMMHC aka Myh1 1) is expressed exclusively by true smooth muscle cells (18) and is distinctly absent from wound myofibroblasts. Lineage tracing in the wounds of SMMHC-CreER$^{T2}$;R26R mice was performed using two induction protocols: 30 days before wounding to label pre-existing VSMCs of the cutaneous blood vessels and their progeny (n=4) (FIG. 13A-B), and between days 11 and 17 after wounding to more specifically label VSMCs of the wound blood vessels (n=4) (FIG. 13C-D). Upon analysis on day 28, lacZ activity remained restricted to wound and peri-wound blood vessels, and in all cases new adipocytes were not labeled.

Next, the progeny of regenerating panniculus carnosus stem cells were traced. Similar to other skeletal muscles, regeneration of panniculus carnosus is dependent on Pax7-expressing satellite stem cells. Intriguingly, a recent study that performed lineage tracing in Pax7-Cre mice concluded that upon wound healing panniculus carnosus satellite progenitors convert into dermal cells, and they constitute nearly a quarter of all cells in the newly formed scar tissue. However, more careful examination of Pax7 promoter activity during development shows that it becomes exclusive to skeletal muscle lineage only after E12.5 and prior to that time point it is broadly active in dermomyotome precursors labeling dorsal dermis. Therefore, to achieve satellite stem cell specificity, lineage tracing was performed using an inducible Pax7-CreER$^{T2}$ model. In Pax7-CreER$^{T2}$;R26R mice that were induced one week prior to wounding robust yet exclusive activation of lacZ expression was observed in the regenerating muscle fibers of the panniculus carnosus at the wound edge with no contribution to the wound scar tissue (n=4) (FIG. 13E).

Next, adipogenic potential of dermal papilla cells from new hair follicles was tested. During wound regeneration dermal papillae form before adipocytes and in SM22-Cre and SMA-CreER$^{T2}$ mice they also activate reporter expression (FIG. 11C, 12A', 15B). In normal hair follicles dermal papillae were reported to contain multipotent progenitors called skin-derived precursors (SKPs) that, among other lineages, can be induced to differentiate into adipocytes. A recent study showed that CD133-CreER$^{T2}$ labeled dermal papilla cells of normal hair follicles do not contribute progeny toward wound scar tissue. To definitively address contribution of dermal papillae from new hair follicles toward new adipocytes, wounding in CD133-CreER$^{T2}$;td-Tomato mice was performed. Although normally CD133-CreER$^{T2}$ is active in dermal papillae during hair follicle development and during first anagen phase of the hair cycle, it becomes largely silenced during catagen and telogen phases. It also remains active in the endothelium of some blood vessels as judged by the expression of endogenous lacZ reporter contained within CD133-CreER$^{T2}$ (FIG. 14A). We show that CD133-CreER$^{T2}$ becomes reactivated in the new hair follicles, providing a genetic tool for specific tracing of new dermal papilla cell progeny in the wound (FIG. 14B). We now show that ten days after the induction of tdTomato expression in new dermal papillae of CD133-CreER$^{T2}$;tdTomato mice, red fluorescent cells continue to be restricted to new dermal papillae and no new adipocytes become labeled (n=7) (FIG. 14C, 14D). Lastly, the adipogenic potential of dermal papilla cells was tested in the context of the so-called hair patch assay, which reproduces aspects of skin and hair follicle organogenesis from dissociated cells. Because neonatal skin contains many committed progenitors, including preadipocytes, patches generated with dissociated unsorted newborn mouse epidermis and dermis result in robust development of both hair follicles and fat (n=12) (FIG. 14E). Newborn mouse dermis was then substituted with vibrissa-derived dermal papilla cells from mice with lacZ knocked into the Retn locus. In these patches, formation of large vibrissa-like follicles and only occasional and always lacZ negative adipocytes were observed (n=4) (FIG. 14G). In contrast, the Retn-lacZ stromo-vascular fraction (SVF) cells were able to form lacZ positive adipocytes within patches (n=12) (FIG. 14F), confirming the lack of adipogenic differentiation potential by dermal papillae cells in the context of hair follicle organogenesis. Taken together, the above lineage tracing studies help to define the in vivo adipogenic potential of various mesenchymal cells in the wound scar and also establish the role of myofibroblasts as the key adipogenic progenitors (FIG. 13F).

Example 4: Differential Gene Expression Dynamics in Cutaneous Wound Myofibroblasts Dermal fraction was isolated from dorsal cutaneous wounds of adult Sm22-Cre;tdTomato mice and viable myofibroblasts were FACS-sorted as Zombie$^{neg}$;tdTomato$^{hi}$ from four post-wounding time points (FIG. 16), including: (1) day 12—initial wound closure and peak of myofibroblast presence, (2) day 15—active formation of new hair follicles, (3) day 21—appearance of Zfp423-expressing dermal progenitors juxtaposed to new hair follicles, and (4) day 26—maturation of new adipocytes.

To resolve the transcriptome of cutaneous wound myofibroblasts, SMART-seq2 was performed on RNAs isolated from viable, uncultured FACS-sorted tdTomato$^{hi}$ to myofibroblasts. To identify unbiased gene expression profile changes in myofibroblasts across cutaneous regeneration, inferential statistical analyses using the two-step regression model algorithm were conducted. Next MaSigPro and identified 4,120 transcripts (approximately 10% of the vM4 gencode gene annotations) that showed statistically significant differential expression across all four time points analyzed (P<0.05) (FIG. 3B). The expression patterns of all differentially expressed genes were analyzed using K-means clustering. These differentially expressed transcripts were grouped into five distinct clusters: (i) 1,412 transcripts in cluster C1 were high on days 12 and decreased by day 21, (ii) 1,244 transcripts in cluster C2 were high on days 12 and 15 and decreased significantly by day 26, (iii) 379 transcripts in cluster C3 transiently increased on days 15 and 21 relative to days 12 and 26, (iv) 688 transcripts in cluster C4 increased on days 21 and 26, and (v) 397 transcripts in cluster C5 increased on day 26 (FIG. 3B). Among the differentially expressed genes, the number of enriched cell cycle regulators significantly decreased during late post-wounding time points (compare small number of genes in clusters C3-C5 vs. these in C1 and C2; FIG. 3C). Similar temporal dynamics (i.e. decrease at late post-wounding time points) were observed for the enriched transcriptional regulators, epigenetic enzymes and inflammatory pathway genes. Contractile genes became downregulated after day 15, consistent with the shutdown of the active contractile state by myofibroblasts during late wound healing stages. The number of enriched extracellular matrix and secreted/signaling pathway genes showed a prominent increase at times coinciding with wound adipogenesis, days 21 and 26 (in cluster C4; FIG. 3C). Principal component analysis (PCA) of differentially expressed genes showed myofibroblasts from individual stages clustering closely together (FIGS. 3A; 17), corroborating that pooled populations of myofibroblasts isolated across wound regeneration display unique and dynamic transcriptomic profiles.

Example 5: Changes in Transcriptional Regulators

Figure 18:
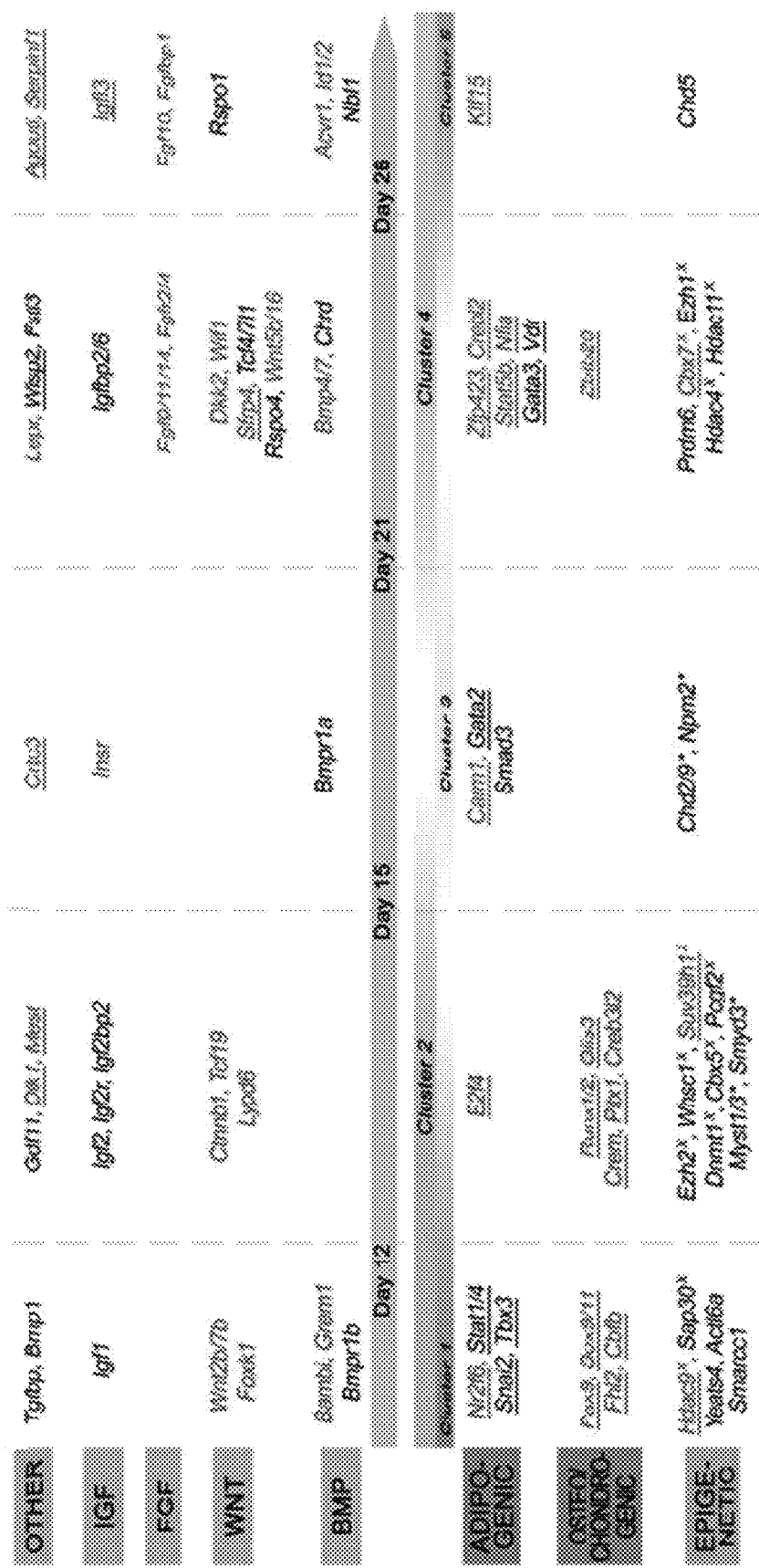
FIG. 18: Gene expression changes in myofibroblasts during wound healing reflect their conversion to adipocytes. Adipogenic inhibitors are highly expressed at early time points whereas, in later time points, activators of adipogenesis are highly expressed.
Figure 22:
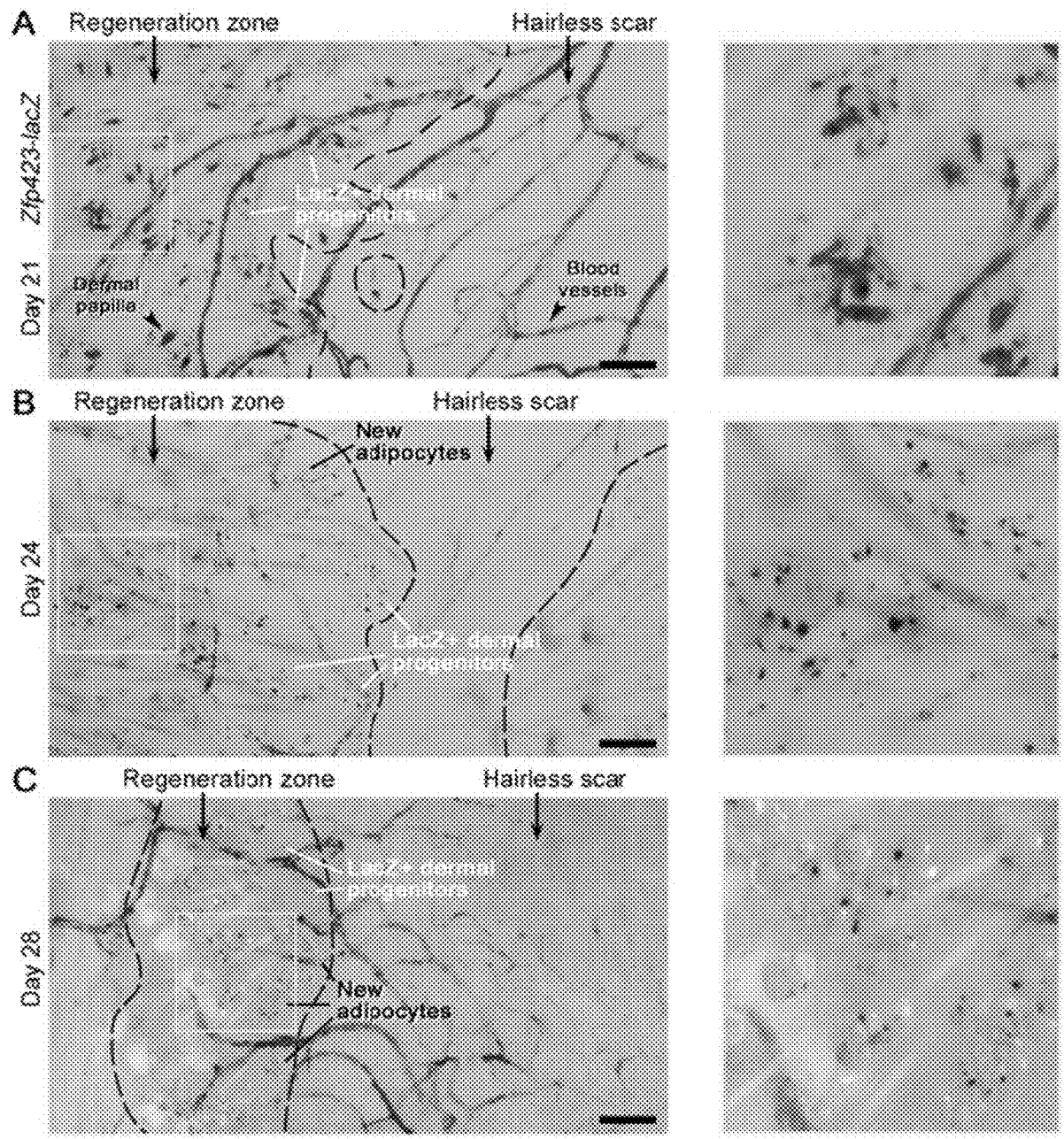
FIG. 22: Details of Zfp423 activity (lacZ expression) in the wounds of Zfp423-lacZ mice. (A) Many lacZ positive cells start to appear in close proximity to new hair follicles on to wound day 21. LacZ is also expressed on wound blood vessels, and by dermal papillae of virtually all new hair follicles (arrowheads). (B) On day 24, lacZ expression persists on dermal progenitors next to new hair follicles and on wound blood vessels. It turns off on dermal papillae of new hair follicles. Additionally, few newly differentiated new adipocytes express lacZ. (C) On wound day 28, the number of lacZ positive wound dermal progenitors sharply decreased, replaced by many lacZ positive mature adipocytes. Expression persists on wound blood vessels. Views of underside of skin. Size bars: A-C—200 µm.

A number of transcriptional regulators previously implicated in adipogenesis show expression changes consistent with the activation of adipogenic lineage commitment at late post-wounding time points (FIG. 18). Known modulators of adipogenesis, including negative regulators Nr2f6 (−1.4x) and E2f4 (−2.1x) were downregulated (clusters C1 and C2 accordingly), while Zfp423 (+2.6x), Crebl2 (+1.9x), Stat5b (+1.7x), and Kfl5 (+2.6x) were upregulated (clusters C4 and C5). Here and below, the day 26 vs. day 12 fold ratio is shown. Concomitant with the above changes in adipose lineage regulators, expression changes were observed for several key transcriptional regulators of alternative mesenchymal lineages, to including chondrogenic and osteogenic (FIG. 22). Prominently downregulated were Sox9 (−2.7x), Sox11 (−2.4x), Fhl2 (−2.4x), Runx1 (−2.9x), Runx2 (−3.2x), Glis3 (−3.3x), and Pitx1 (−2.1x). Of note, key transcriptional regulators of the myogenic lineage, Pax3, Pax7, Myf5, Myf6, and Myod were not differentially expressed (P<0.05).

Example 6: Changes in Major Signaling Pathways

The above-described changes in transcriptional regulators were accompanied by substantial changes in several major signaling pathways associated with adipose lineage regulation (FIG. 18). Signaling members of the pro-adipogenic Bone Morphogenic Protein (BMP) pathway showed changes consistent with BMP activation at late post-wounding stages, on days 21-26. Prominently, BMP antagonists Bambi (−1.6x) and Grem1 (−3.5x) were downregulated (cluster C1), while BMP ligands Bmp4 (+5.0x) and Bmp7 (+7.4x) became upregulated (cluster C4). Id1 (+2.0x) and 1d2 (+1.7x), known direct BMP targets, also were upregulated on day 26 (cluster C5). Also, BMP receptor Bmpr1a was transiently upregulated on days 15 and 21 (cluster C3).

Opposite dynamics were observed for the members of the canonical WNT signaling pathway, which is largely associated with the inhibition of adipogenesis (FIG. 18). WNT ligands, Wnt2b (−3.&r) and Wnt7b (−1.2x) became downregulated (cluster C1), while soluble WNT antagonists Dkk2 (+14.3x), Wifl (+32.5x) and Sfrp4 (+2.3x) became upregulated during late post-wounding stages (cluster C4). Inhibitory effect of Sfrp4 on adipogenesis has been previously demonstrated in vitro. Furthermore, downregulated during late stages were the intracellular signaling mediators of WNT, including Foxk1 (−1.5x), Cmtnnb1 (−1.3x), Tcf19 (−2.1x) and Lypd6 (−1.9x). Importantly, higher levels of canonical WNT signaling on days 12-15 are consistent with earlier reports on the activation of canonical WNT signaling in wound myofibroblasts at the onset of new hair follicle regeneration. At late stages (cluster C4), an upregulation of Wnt5b (+2.7x) and Wnt16 (+3.4x), both of which have been show to act as non-canonical WNT ligands, was also observed. Promoting effect of non-canonical WNT signaling on adipogenesis, in particular Wnt5b, has been documented in vitro. Among other pathways (FIG. 18), Fibroblast Growth Factor (FGF) pathways show distinct gene expression patterns during late stages. Several FGF ligands were upregulated, including Fgf9 (+3.6x), Fgf11 (+1.7x), Fgf14 (+1.9x) in cluster C4 and Fgf10 (+3.1x) in cluster C5. Also upregulated were FGF receptors Fgfr2 (+3.0x) and Fgfr4 (+5.7x) in cluster C4 and FGF binding protein Fgfbp1 (+11.3x) in cluster C5. Previously, Fgf10 has been shown to stimulate proliferative expansion of adipose progenitors. Dynamic changes are also observed for the Insulin/Insulin Growth Factor (IGF) signaling pathway. Prominently, ligand Igf2 (−19.&r), its receptor Igf2r (−2.1x) and modulator of translation Igf2bp2 (−4.1x) became downregulated in late stages (cluster C2). In line with these observations, previous reports suggest that a decrease in Igf2 levels is associated with increased fat deposition and occasional obesity. Moreover, Igf2 inactivation, along with Myod (not differentially expressed), was shown to be essential for brown fat vs. skeletal muscle cell fate selection.

Among other established and differentially expressed regulators of adipogenesis (FIG. 18), Dlk1 (−10.5x) (76-82) and Mest (−23.9x), known negative regulators, were downregulated (cluster C2), while Agouti (+2.2x), known positive regulator, was upregulated (cluster C5). Also prominently upregulated in clusters C4 was adipokine Wisp2 (+21.3x), known to be highly expressed by adipose precursor cells. Wisp2 has been shown to play a critical role in mediating BMP-induced adipogenic commitment of mesenchymal progenitor cells by shuttling Zfp423 into the nucleus.

Example 7: Changes in the Epigenetic Regulators

A number of changes are also observed in the expression of known epigenetic enzymes (FIG. 18). Numerous epigenetic enzymes broadly associated with global transcriptional repression were downregulated during late time points. These include histone deacetylase Hdac9 (−2.1x) and histone deacetylase complex subunit Sap30 (−4.5x). Also downregulated were several histone methyltransferases, including Ezh2 (−2.4x), the key catalytic subunit of the Polycomb repressive complex 2, and Whscl (−3.4x), both of which catalyze deposition of the repressive H3K27me marks (mono-, di-, and tri-), and Suv39h1 (−2.9x), which catalyzes deposition of the repressive H3K9me3 marks. Other downregulated transcriptional repressors were polycomb group ring finger protein Pcgf2 (−2.1x), chromobox protein homolog Cbx5 (−2.2x), and prominently, DNA methyltransferase Dnmt1 (−2.3x). Among these factors, inhibitory effects during adipogenesis were shown for Hdac9 (89-92) and Suv39h1. Dnmt1 was shown to become downregulated during adipocyte differentiation in vitro, and its siRNA-mediated knockdown in preadipocytes induces premature differentiation. Among other epigenetic modifiers with at least two-fold change in expression were putative histone methyltransferase Prdm6 (+2.5x) in cluster C4 and chromatin remodeling protein Chd5 (+2.6x) in cluster C5.

Example 8: Meta-Analysis of Myofibroblasts' Transcriptome Profile

Figure 19:
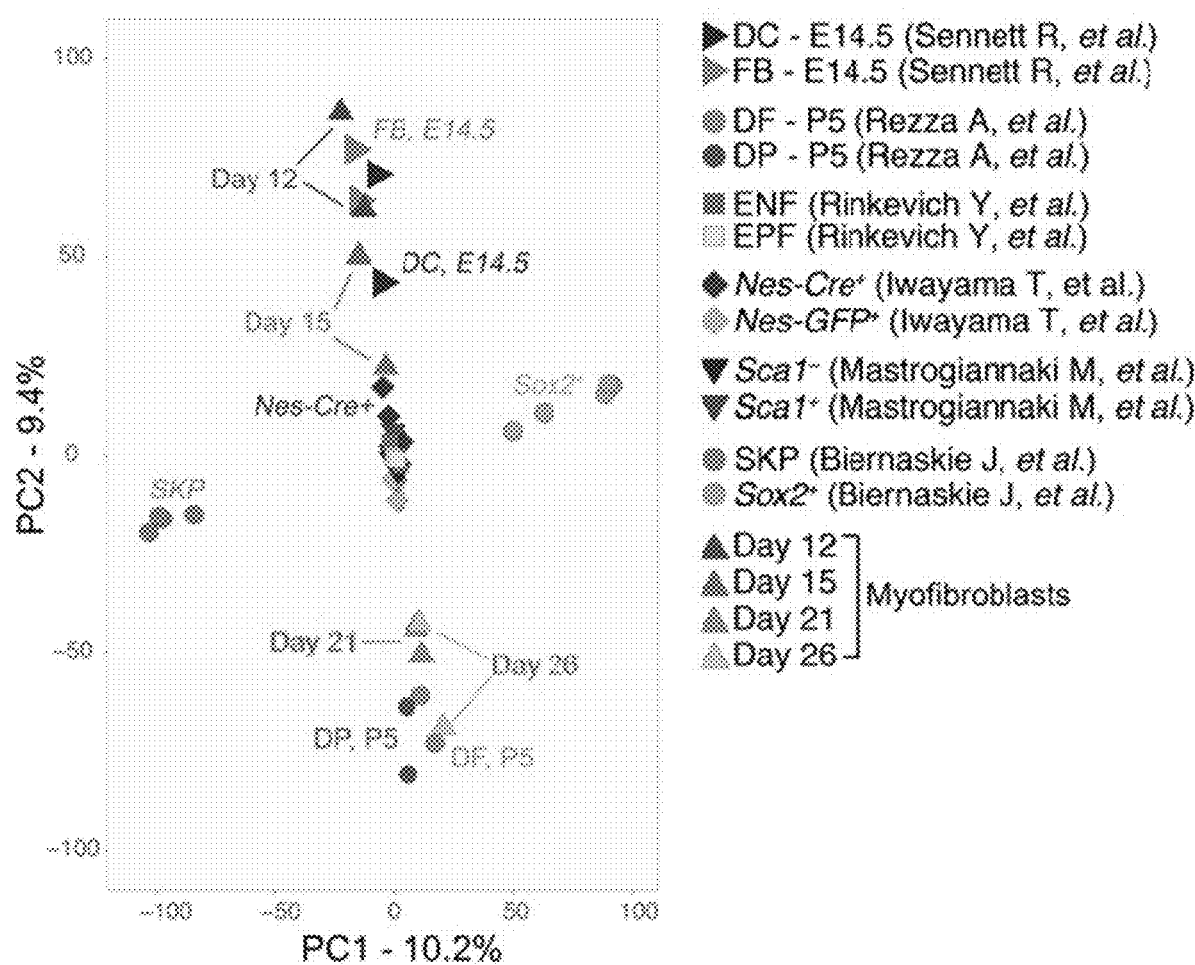
FIG. 19: Transcriptome-wide meta-analysis of wound myofibroblasts and dermal cells from unwounded skin. Transcriptome-wide comparison between myofibroblasts from days 12, 15, 21 and 26 (green triangles) and previously reported dermal cell populations (see "Meta-analyses" section of the Materials and methods for technical details). Analysis reveals that wound day 12 and 15 myofibroblasts cluster the closest to E14.5 dermal fibroblasts (DF) and dermal condensate (DC) cells (dark and light purple triangles), while wound day 21 and 26 myofibroblasts cluster near P5 dermal fibroblasts (DF) (light blue circles). Wound myofibroblasts at all time points are distinct from the reported primary passaged skin-derived precursor (SKP) cells (dark orange circles) and sorted Sox2-GFP$^+$;CD34$^{neg}$ (Sox2$^+$) neonatal dermal cells (light orange circles).

To gain further insight into the possible relation between wound myofibroblasts and dermal cells from unwounded skin, the RNA-seq profiles of myofibroblasts were compared with previously reported RNA-seq and microarray data sets from various dermal cell populations using principal component analyses (PCA) (see "Meta-analyses" section of Example 1 for details) (FIG. 19). Close association between Nes-Cre$^+$/Nes-GFP$^+$ subcutaneous fat pericytes, P56 Engr$^+$/EngF$^{neg}$ dermal fibroblasts, and P2 Sca1$^+$/Sca1$^{neg}$ reticular and papillary dermal fibroblasts was observed, suggesting negligible variance between their transcriptomes, but otherwise significant transcriptome variance relative to other dermal cells, including wound myofibroblasts from all time points. Recently, Engr$^+$ fibroblasts (EPFs), but not Engr$^{neg}$ fibroblasts (ENFs) were shown to be the predominant type of scar-forming fibroblasts in small excisional skin wounds in adult mice. The PCA suggests significant transcriptome variance between myofibroblasts in large wounds and Engr$^+$/Engr$^{neg}$ dermal fibroblasts, suggesting that myofibroblasts undergo significant transcriptome changes following wounding. Sca1$^+$ reticular dermal fibroblasts were recently described as having a pre-adipocyte gene signature, validated in vitro by their ability to undergo adipocyte differentiation. Significant transcriptome variance between myofibroblasts and Sca1$^+$ dermal cells does not support a close relationship.

Myofibroblasts were also compared to skin-derived precursors (SKPs) and Sox2$^+$ dermal papilla cells (the primary source of SKPs in adult mouse skin). Both SKPs and Sox2$^+$ dermal papilla cells were reported to be multipotent based on their ability to differentiate in vitro and in cell transplantation assays into several mesenchymal cell types, including adipocytes, as well as several types of neuronal cells, peripheral neurons and Schwann cells. However, a recent study and our lineage studies (see Example 3 above) show no contribution from pre-existing and new dermal papilla cells toward wound scar tissue and new adipocytes. In parallel, high transcriptome variance was also seen between SKPs, Sox2$^+$ dermal papilla cells and myofibroblasts from all time points. Together, the lineage tracing and reconstitution patch assays (FIG. 14) coupled with transcriptome-wide meta-analyses (FIG. 19) suggest that multipotent precursors of the dermal papilla are the unlikely source of new adipocytes.

Importantly, on PCA analysis, E14.5 dermal fibroblasts (DFs) and dermal condensate cells (DCs) cluster in close proximity to day 12 and 15 myofibroblasts, while P5 dermal fibroblasts cluster close to day 21 and 26 myofibroblasts. These results are in line with the notion that: (i) the transcriptomes of myofibroblasts in adult regenerating wounds undergo changes similar to these in dermal fibroblasts during skin morphogenesis, and (ii) that wound myofibroblasts reprogram toward a distinct regeneration-competent state.

Example 9: Adipogenic Conversion of Human Scar Fibroblasts In Vitro

Figure 26:
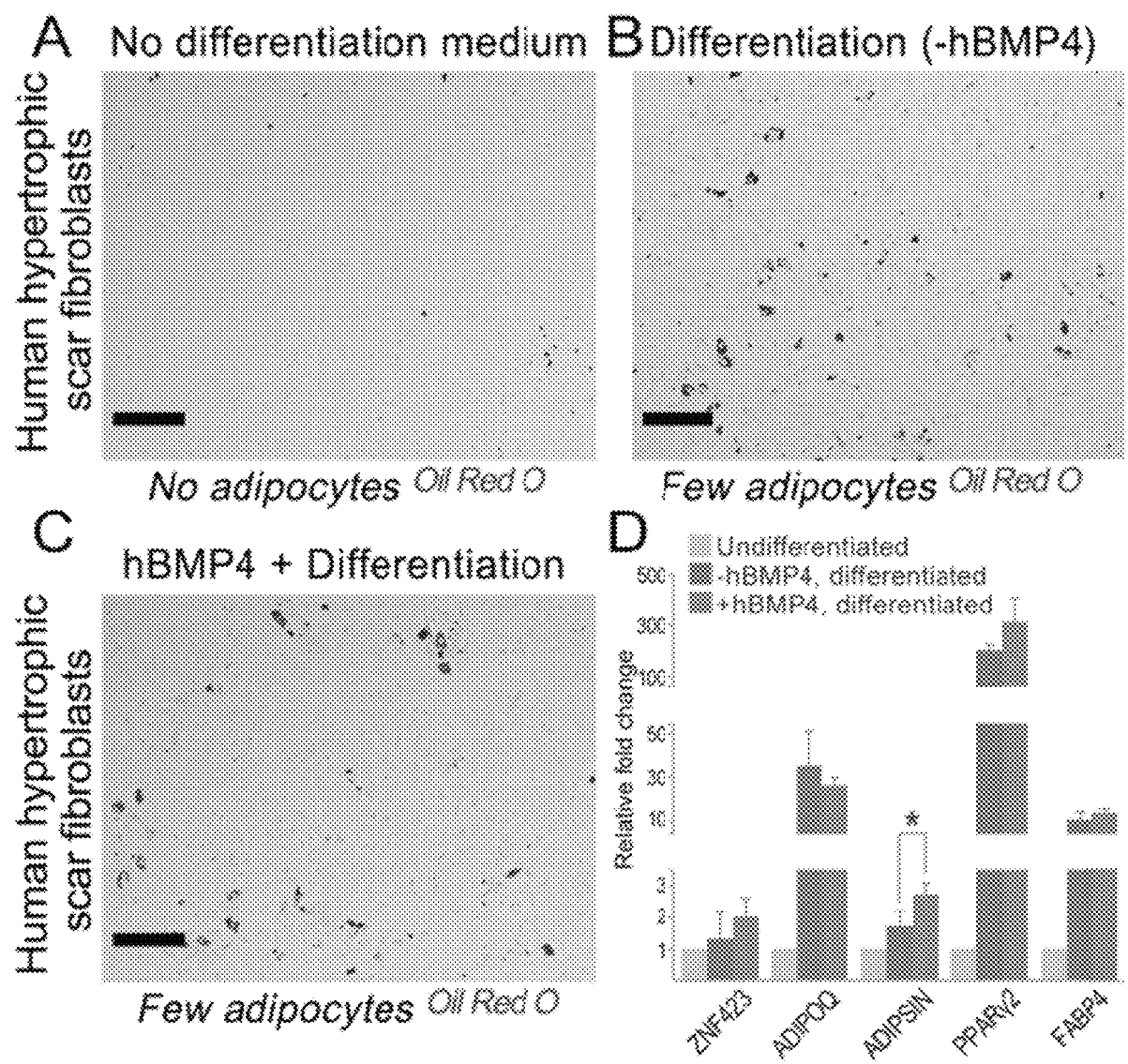
FIG. 26: Adipogenic differentiation of human hypertrophic scar fibroblasts. In vitro treatment of cells with hBMP4 prior to differentiation does not induce an increase in adipogenic potential in human hypertrophic scar fibroblasts (C) as compared to non-hBMP4 control (B). No adipocytes formed without differentiation media (A). Cells are stained for Oil Red O. (D) qRT-PCR against select adipogenic genes shows that only ADIPISIN becomes significantly upregulated following hBMP4 treatment (n=3). Size bars: A-C—200 µm.

Human cells derived from keloid (n=3) and hypertrophic scars (n=3; Table 2) were subjected to adipogenic culture (see Materials and methods). Cells were pre-treated with to hBMP4 for 48 hours in an attempt to induce BMP-mediated adipogenic commitment, and then differentiated using standard adipogenic cocktail. As judged by the appearance of Oil Red O positive cells with typical adipocyte morphology, these culture conditions consistently induced adipogenic conversion of keloid (FIG. 4C), but not hypertrophic scar cells (FIG. 26). Adipogenic conversion of keloid scar fibroblasts was accompanied by the upregulation of adipogenic genes, ZNF423 (human Zfp423 homolog), ADIPOQ, ADIPOSIN, PPARG2, FABP4 (FIG. 4D). Importantly, adipogenic potential of both hypertrophic and keloid scar cells without hBMP4 treatment was low. Next, to test if anagen hair follicles are sufficient to induce adipogenic conversion of human keloid cells, they were co-cultured with freshly microdissected human scalp anagen hair follicles for five days prior to inducing adipogenic differentiation. To prevent possible contamination of keloid cell culture with hair follicle-derived cells, the latter were cultured on top of an insert that prevents cell migration (see Materials and methods). We show that hair follicle co-culture is sufficient to substitute for hBMP4 and it induces adipogenic conversion of keloid cells, as judged by the formation of BODIPY-positive lipid-containing adipocytes (FIG. 4E) and activation of adipogenic gene expression (FIG. 4F). Together, these results indicate partial conservation of the BMP/Zfp423 adipogenic reprogramming pathway in human keloid scar cells and also show that hair follicles are sufficient to induce adipogenic reprogramming.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method for treating wound healing pathologies or for inhibiting or suppressing a fibrotic skin disorder in a subject having a wound healing pathology or fibrotic skin disorder, the method comprising the step of administering to the subject a composition consisting of therapeutically effective amount of a wild-type bone morphogenetic protein 2 (BMP2) polypeptide, or a wild-type bone morphogenetic protein 4 (BMP4) polypeptide, or a combination thereof.

2. The method of claim 1, wherein said wound healing pathology or said fibrotic skin disorder is atrophic scars (AS), hypertrophic scars (HS), keloid scars (KS), or another condition characterized by abnormal proliferation of mesenchymal scar tissue.

3. The method of claim 2, wherein said step of administering is performed during spreading stage of scar formation.

4. The method of claim 1, wherein said step of administering is via topical administration.

5. The method of claim 1, wherein said step of administering is via intradermal or subepidermal administration.

6. The method of claim 1, further comprising the step of administering a corticosteroid to the subject.

7. The method of claim 6, wherein the corticosteroid is administered by intralesional injection.

8. The method of claim 1, wherein the composition comprises a human wild-type bone morphogenic protein 4 (hBMP4).

9. The method of claim 1, wherein the composition is in aqueous solution or suspension at from about 6 ng/ml to about 25 ng/mL.

10. The method of claim 8, wherein the composition is in aqueous solution or suspension at from about 6 ng/ml to about 25 ng/mL.

* * * * *